(12) United States Patent
Gupta et al.

(10) Patent No.: US 9,045,780 B2
(45) Date of Patent: Jun. 2, 2015

(54) PROCESS FOR THE STEREOSELECTIVE ENZYMATIC REDUCTION OF KETO COMPOUNDS

(75) Inventors: Antje Gupta, Wiesbaden (DE); Maria Bobkova, Wiesbaden (DE); Anke Tschentscher, Eltville-Hattenheim (DE)

(73) Assignee: IEP GMBH, Wiesbaden (DE)

(*) Notice: Subject to any disclaimer, the term of this patent is extended or adjusted under 35 U.S.C. 154(b) by 20 days.

(21) Appl. No.: 13/254,820

(22) PCT Filed: Mar. 3, 2010

(86) PCT No.: PCT/EP2010/052701
§ 371 (c)(1),
(2), (4) Date: Oct. 28, 2011

(87) PCT Pub. No.: WO2010/100195
PCT Pub. Date: Sep. 10, 2010

(65) Prior Publication Data
US 2012/0040425 A1    Feb. 16, 2012

(30) Foreign Application Priority Data
Mar. 5, 2009    (EP) .................................... 09450050

(51) Int. Cl.
| | | |
|---|---|---|
| *C12P 7/22* | (2006.01) | |
| *C12N 9/02* | (2006.01) | |
| *C12P 7/42* | (2006.01) | |
| *C12P 7/02* | (2006.01) | |
| *C12P 7/06* | (2006.01) | |
| *C12P 7/16* | (2006.01) | |
| *C12P 7/18* | (2006.01) | |

(52) U.S. Cl.
CPC ................. *C12P 7/42* (2013.01); *C12N 9/0004* (2013.01); *C12P 7/02* (2013.01); *C12P 7/06* (2013.01); *C12P 7/16* (2013.01); *C12P 7/18* (2013.01); *C12P 7/22* (2013.01); *Y02E 50/17* (2013.01); *Y02E 50/10* (2013.01)

(58) Field of Classification Search
CPC ................ C12P 7/22; C12P 7/26; C12P 7/16; C12P 7/62; C12N 9/004
USPC .......................... 435/156, 160, 148, 155, 189
See application file for complete search history.

(56) References Cited

U.S. PATENT DOCUMENTS

2009/0221044 A1* 9/2009 Gupta et al. .................. 435/135

FOREIGN PATENT DOCUMENTS

| WO | 02/12544 A2 | 2/2002 |
|---|---|---|
| WO | 02/086126 A2 | 10/2002 |
| WO | 2006/087235 A1 | 8/2006 |
| WO | 2007/012428 A1 | 2/2007 |
| WO | 2007/073875 A1 | 7/2007 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., (Structure, 2002, vol. 10: 8-9.*
International Search Report dated Jul. 5, 2010 as received in related application No. PCT/EP2010/052701.
Database UniProt [Online] 1-10 Jun. 1, 2003, "SubName: Full=Short chain dehydrogenase;" XP002541641 retrieved from EBI accession No. UNIPROT:081AU6 Database accession No. 081AU6 the whole document.
Database UniProt [Online] Aug. 22, 2006, "SubName: Full=Short-chain dehydrogenase/reductase SDR; Flags: Precursor;" XP002541642 retrieved from EBI accession No. UNIPROT:011G59 Database accession No. 011G59 the whole document.
Jornvall H et al: "SDR and MDR: completed genome sequences show these protein families to be large, ,of old origin, and of complex nature" FEBS Letters, Elsevier, Amsterdam, NL, vol. 445, No. 2-3, Feb. 26, 1999, pp. 261-264, XP004259268 ISSN: 0014-5793 abstract p. 261, col. 2, paragraph 3 —paragraph 4 p. 263, col. 1, paragraph 3 —col. 2, paragraph 1 figure 1; table 1.
Oppermann U C T et al: "Structure-Function Relationships of SDR Hydroxysteroid Dehydrogenases" Advances in Experimental Medicine and Biology, Springer, US, vol. 414, Jan. 1, 1997, pp. 403-415, XP008012012 ISSN: 0065-2598 p. 403 figure 3; tables 1,3.
Joernwall H et al: "Short-Chain Dehydrogenases/Reductases (SDR)" Biochemistry, American Chemical Society, Easton, PA.; US, vol. 34, No. 18, May 9, 1995, pp. 6003-6013, XP000929805 ISSN: 0006-2960 abstract p. 6005, col. 2, paragraph 2 p. 6007, col. 1, paragraph 2—p. 6009, col. 1, paragraph 2 p. 6010, col. 2, paragraph 2—p. 6011, col. 1, paragraph 1 figures 1,5.

* cited by examiner

*Primary Examiner* — Tekchand Saidha
*Assistant Examiner* — Md. Younus Meah
(74) *Attorney, Agent, or Firm* — Maschoff Brennan

(57) ABSTRACT

In a process for the stereoselective, in particular enantioselective enzymatic reduction of keto compounds to the corresponding chiral hydroxy compounds, wherein the keto compounds are reduced with an enantioselective, NADH-specific oxidoreductase, a polypeptide is used for reducing the keto compounds, which polypeptide exhibits an R-ADH-signature H-[P; A]-[I; A; Q; V; L]-[G; K]-R at positions 204-208 and the following further structural features in their entirety:
(i) an N-terminal Rossmann-Fold GxxxGxG,
(ii) an NAG-motif at position 87,
(iii) a catalytic triad consisting of S 139, Y 152 and K 156,
(iv) a negatively charged amino acid moiety at position 37,
(v) two C-terminal motifs in the dimerization domain [A; S]-S-F and [V; I]-DG-[G; A]-Y-[T; C; L]-[A; T; S]-[Q; V; R; L; P],
(vi) Val or Leu at position 159 (4 positions downstream of K 156),
(vii) Asn at position 178, and
(viii) a proline moiety at position 188.

8 Claims, No Drawings

PROCESS FOR THE STEREOSELECTIVE ENZYMATIC REDUCTION OF KETO COMPOUNDS

The present invention relates to a process for the stereoselective, in particular enantioselective enzymatic reduction of keto compounds to the corresponding chiral hydroxy compounds, wherein the keto compounds are reduced with an enantioselective, NADH-specific oxidoreductase. The invention relates in particular to the use of selected oxidoreductases in this process.

Optically active hydroxy compounds are valuable chirons with broad applicability for the synthesis of pharmacologically active compounds, aromatic substances, pheromones, agricultural chemicals and enzyme inhibitors. Thereby, an increasing demand for chiral compounds and thus chiral synthesis technologies can be noted particularly in the pharmaceutical industry, since, in the future, racemic compounds will hardly be used as pharmaceutical preparations.

The asymmetric reduction of prochiral keto compounds is a sector of stereoselective catalysis, wherein biocatalysis constitutes a powerful competitive technology versus chemical catalysis. The chemical asymmetric hydrogenation requires the use of highly toxic and environmentally harmful heavy metal catalysts, of extreme and thus energy-intensive reaction conditions as well as large amounts of organic solvents. Furthermore, these methods are often characterized by side reactions and insufficient enantiomeric excesses.

In nature, reductions of prochiral keto compounds to hydroxy compounds and oxidations proceeding inversely occur in numerous biochemical pathways, both in the primary metabolism and in the secondary metabolism, in every organism and are catalyzed by different types of secondary alcohol dehydrogenases (ADH) and oxidoreductases. Normally, these enzymes are cofactor-dependent.

In various sequencing projects, numerous amino acid sequences have, in each case, been identified for different organisms, which are presumably oxidoreductases of an unknown activity, function and enantio- and chemoselectivity, respectively. The basic suitability of oxidoreductases for use in industrial processes could recently be demonstrated on the basis of numerous examples.

Recently, it has been possible to show that the use of isolated oxidoreductases in aqueous/organic two-phase systems with organic solvents is extremely efficient, economical and feasible also at high concentrations (>5%). In the described systems, the keto compound to be reduced, which usually is poorly soluble in water, thereby forms the organic phase together with the organic solvent. Also, the organic solvent itself can partly be dispensed with. In that case, the organic phase is formed from the keto compound to be reduced (EP 1 383 899). Coenzyme regeneration is realized by the concurrent oxidation of secondary alcohols, for which, in most cases, the inexpensive water-miscible 2-propanol is used (WO 2006/087235). The use of 2-methyl-4-pentanol or 2-octanol for the regeneration of the cofactors NADH or NADPH is likewise advantageous (WO 2007/036257).

Numerous oxidoreductases of different specificities and selectivities can be found in the patent literature of recent years. Various examples can be found for S-specific oxidoreductases and dehydrogenases of high enantioselectivity, which, almost without exception, use NADH as a cofactor and thus can be used very economically under the above-described process conditions. Examples of such S-specific oxidoreductases are carbonyl reductases from *Candida parapsilosis* (CPCR) (U.S. Pat. No. 5,523,223 and U.S. Pat. No. 5,763,236; Enzyme Microb. Technol. 1993 November; 15(11):950-8) and *Pichia capsulata* (DE 10327454.4), carbonyl reductases from *Rhodococcus erythropolis* (RECR) (U.S. Pat. No. 5,523,223), *Norcardia fusca* (Biosci. Biotechnol. Biochem., 63(10) (1999), p. 1721-1729; Appl. Microbiol. Biotechnol. 2003 September; 62(4):380-6; Epub 2003 Apr. 26) and *Rhodococcus ruber* (J. Org. Chem. 2003 Jan. 24; 68(2):402-6). Furthermore, S-specific carbonyl reductases from *Rhodotorula mucillaginosa, Microbacterium* spec., *Gordonia rubripertincta, Pichia stipitis* and *Pichia trehalophila* (WO 2007/012428) are described.

Examples of R-specific secondary alcohol dehydrogenases are identified from organisms of the genus *Lactobacillus*: *Lactobacillus kefir* (U.S. Pat. No. 5,200,335), *Lactobacillus brevis* (DE 19610984 A1; Acta Crystallogr. D Biol. Crystallogr. 2000 December; 56 Pt 12:1696-8), *Lactobacillus minor* (DE 10119274) and *Leuconostoc carnosum* (WO 2007/012428). All these enzymes have the disadvantage that NADPH is required as a cofactor, which is substantially more expensive than NADH and thus involves relatively high process costs.

"R-specific" oxidoreductases are understood as those which reduce unsubstituted carbonyl compounds, such as, for example, 2-butanone, 2-octanone or acetophenone, to the corresponding R-hydroxy compounds, i.e., R-2-butanol, R-2-octanol and R-2-phenyl ethanol. 4-Halo-3-oxobutyric acid ester, for example, is reduced to S-4-halo-3-hydroxybutyric acid ester by R-specific oxidoreductases.

"S-specific oxidoreductases" are ADH which reduce unsubstituted carbonyl compounds, such as, for example, 2-butanone, 2-octanone or acetophenone, to the corresponding S-hydroxy compounds, i.e., S-2-butanol, S-2-octanol and S-2-phenyl ethanol. 4-Halo-3-oxobutyric acid ester, for example, is reduced to R-4-halo-3-hydroxybutyric acid ester by S-specific oxidoreductases.

In the present application, by the term "specific" is understood that the corresponding enantiomer is formed by >95%.

Furthermore, a number of unspecific NADPH-dependent enzymes from yeasts of the genus *Candida magnoliae* are described in the most recent patent literature (EP 1152054 A1, WO 2007/033928, WO 2006/046455, WO 2005/033094). Besides their NADPH-dependence, they have the major disadvantage that they cannot be used in processes with a substrate-coupled coenzyme regeneration, but always require a second enzyme system for the coenzyme regeneration. Glucose dehydrogenase with glucose as a cosubstrate is preferably used for this purpose. In addition, these enzymes have the disadvantage that they are normally unspecific, i.e., the reduction of unsubstituted carbonyl compounds, such as, for example, 2-butanone, 2-octanone or acetophenone, normally leads to racemic alcohols; only in exceptional cases, these enzymes operate selectively. Therefore, the enatioselective reduction of substrates such as 4-halo-3-oxobutyric acid ester, 3-oxoesters or aliphatic ketones, e.g., 2-octanone, is normally not possible with these enzymes.

Only a very limited number of robust, NADH-dependent and clearly R-specific oxidoreductases which are usable in processes with a substrate-coupled coenzyme regeneration with secondary alcohols, preferably 2-propanol, as cosubstrates are available.

A NADH-dependent R-specific oxidoreductase is identified, for example, from *Pichia finlandica* (EP 1179 595 A1). However, it exhibits a very small activity with 2-propanol and hence is unsuitable for processes with a substrate-coupled coenzyme regeneration.

Two further NADH-dependent R-specific oxidoreductases from *Pichia farinosa* and *Candida nemodendra* are described in WO 2007/012428. It has been possible to show therein for the enzyme from *Pichia farinosa* that a coenzyme regeneration with 2-propanol is also possible, but only at concentrations of up to 15% (v/v) isopropanol.

Furthermore, NADH-dependent enzymes from *Leifsonia* (U.S. Pat. No. 7,172,894 B2, Biosci. Biotechnol. Biochem., 70 (2), 2006, pages 418-426) and *Devosia* (WO 2004/027055) are known, wherein at least the enzyme from *Leifsonia* should be R-specific and capable of a substrate-coupled coenzyme regeneration.

However, the oxidoreductases known today, in particular the clearly R-specific enzymes, are not nearly sufficient for exploiting the entire market potential of stereoselective reductions of keto compounds. On the one hand, this can be explained by the fact that the individual enzymes have very different properties with respect to substrate spectrum, pH optimum as well as temperature and solvent stabilities, which often supplement each other. Therefore, even relatively similar homologous enzymes may exhibit a completely different conversion behaviour with regard to one particular substrate. On the other hand, not nearly all of the enzymes described are cloned and overexpressible to a sufficient extent, which means that these enzymes are not available for industrial use.

For exploiting the synthetic potential of the enzymatic asymmetric hydrogenation as extensively as possible, it is therefore necessary to be in possession of a portfolio of different industrially accessible oxidoreductases which is as broad as possible. Meanwhile, the requirements for enzymes which advantageously are usable industrially can be clearly defined.

Therefore, it is the object of the present invention to identify and provide stable, NADH-dependent and R-specific oxidoreductases which are suitable for processes for the reduction of keto compounds to chiral alcohols, using a substrate-coupled coenzyme regeneration.

For this purpose, it is necessary to provide oxidoreductases with a stability as high as possible against secondary alcohols, in particular against isopropanol. Moreover, the enzymes to be provided should be characterized by good expressibility in *Escherichia coli* (>500 units/g *E. coli* wet biomass).

Due to the high demand made on stability and expressibility in *E. coli*, it has been assumed in the present invention that bacterial enzymes are to be preferred over enzymes from yeast.

Furthermore, it is the object of the present invention to identify amino acid sequences and gene sequences, respectively, which, in a recombinantly expressed state, constitute stable NADH-dependent, (R)-specific oxidoreductases and are suitable in process engineering if an enzyme-coupled coenzyme regeneration is used.

The inventors have found that such sequences generally exhibit the known features of a "short-chain" dehydrogenase, such as, e.g., an N-terminal Rossmann-Fold GxxxGxG for cofactor binding, an NAG-motif at position 87 which provides for a stabilization of the central β-pleated sheet structure and a highly conserved catalytic triad consisting of S 139, Y 152 and K 156 in the active centre. For the purposes of the present application, the numerical allocation of individual homologous amino acid moieties in the protein sequences is carried out by the "multi-way protein alignment algorithm" with Score Matrix BLOSUM62 and the 3alpha, 20beta-hydroxysteroid dehydrogenase from *Streptomyces hydrogenans*, Accession Code 2bhd_Strex as a reference.

With the plurality of amino acid sequences available on the internet which exhibit this signature, a definition of further features was required in order to restrict this sequence pool. The inventors therefore claimed that (R)-specific oxidoreductases having the described properties would have to exhibit, in addition, the following sequence features and patterns:

a negatively charged amino acid moiety at position 37 two C-terminal motifs in the dimerization domain: [A; S]-S-F and [V; I]-DG-[G; A]-Y-[T; C; L]-[A; T; S]-[Q; V; R; L; P]

an R-ADH-signature at positions 204 to 208: H-[P; A]-[I; A; Q; V; L]-[G; K]-R

Val or Leu at position 159 (4 positions downstream of K 156)

Asn at position 178 a proline moiety at position 188.

According to this pattern, the following sequences without an existing functional classification were selected from the sequence pool accessible from sequencing projects, were cloned and characterized with regard to their functions.

TABLE 1

| SEQ ID NO | Origin | Length | Accession no. | Closest homologues |
|---|---|---|---|---|
| SEQ ID NO:1 | Bacillus cereus ATCC 14579 | 247 aa | NP-833194 | Glucose-1-dehydrogenase from Lysinibacillus 59% identity |
| SEQ ID NO:2 | Methylibium petroleiphilum Pm1 | 257 aa | YP-001020081 | Short-chain dehydrogenase Flavobacterium 59% identity |
| SEQ ID NO:3 | Mesorhizobium sp. | 251 aa | YP-676781 | Putative oxidoreductase Sinorhizobium 62% identity |
| SEQ ID NO:4 | Streptomyces coelicolor | 263 aa | NP-631416 | short-chain dehydrogenase Comamonas testosteroni 57% identity |
| SEQ ID NO:5 | Ralstonia | 253 aa | YP-299653 (epimerase/dehydratase/ reductase SDR) | short-chain dehydrogenase Bacillus 54% identity |
| SEQ ID NO:6 | Herpentosiphon aurantiacus ATCC 23779 | 252 aa | YP-001544828 | short-chain dehydrogenase Comamonas testosteroni 54% indentity |
| SEQ ID NO:7 | Paracoccus denitrificans | 249 aa | ZP-00631061 | short-chain dehydrogenase, Pedobacter 57% identity |

TABLE 1-continued

| SEQ ID NO | Origin | Length | Accession no. | Closest homologues |
|---|---|---|---|---|

```
2bhd_Strex    1  -----------mhdltgkn--viitggarglgaeaarqavaagahvlitq
Seq ID No 1   1  --------------mklkdkvaiitggasgigestvrlfieegakvviaq
Seq ID No 2   1  ---------mgrvd----nkvalvtggakgigrasalmlaregarvvltq
Seq ID No 3   1  -----------mtgefkdkvalvtgagsgigaaiatelatggaelvvaq
Seq ID No 4   1  msttgttpattgyaaefagrtalvtgaasgiglatarrlgaggarvvvaq
Seq ID No 5   1  ----------meyidmklkdkvaivtggasgigeatvrlfasqgasvvviaq
Seq ID No 6   1  ---------mnqydfrgkvalvtggasgigaacvhtfargqakvyaiyq
Seq ID No 7   1  -----------mdirfdnkialvtgagsglgeialelaasgatvyaaq 2bhd_Strex   38  vldddg-enaarel---gdrarflhhdvtseedwsraadfavtefgalhg
Seq ID No 1  37  fser--gkelsdelnahgyntlfiktdvtkeadikqlihetvstygkidi
Seq ID No 2  38  veeaqgsa-vakeieraggkalfltqdvtdesrwvevvekaraqfggkni
Seq ID No 3  39  lere-sanriveqgirasggrahafavdvadaeavermvdfavrtcgdlhl
Seq ID No 4  51  fnae-gaekaaaelraggveaaaveldvtrpesveaavgfavdtfgskdi
Seq ID No 5  42  rsal--geklarelsesslaahysevdvsreddtrrlidddtvsrfgrldi
Seq ID No 6  40  rnqdlgaqtvaa-vreaggdaiflpvdvaqsgaveamvtdtitafggqldi
Seq ID No 7  39  lhea-taratadrivaaggkakavagdvsdpdavrkaveva-kglggihl 2bhd_Strex   84  lvnnagis-tgtplesesvdhfrkvldvnltgvfigmktvvpa-lkeagg
Seq ID No 1  85  myanagvad-dapanelsyekwkrttdinlsgvflsdkysteqflkqgtg
Seq ID No 2  87  vvnnagig-tagsaedetleawrrlmsvnldgvflgtkhairam-kngpg
Seq ID No 3  88  avnnagiggpseptadypldgwrkvidvmlngvfygmkyeiaailksg-g
Seq ID No 4 100  avnnagiggpgaptgeydvaayqryvrtnldgvfysmryelpaieaaqkg
Seq ID No 5  90  myanagiahpgapvedvsveqwqqmidvmltgvflsnklaivqmkkqgtg
Seq ID No 6  89  avnnagiggesnptgtysiegwqtvidvmlngvfycmryetpamlaqg-g
Seq ID No 7  87  lvnnagiggpsapvgdypldgwkkvidvmlnavfygmrygipamldag-g 2bhd_Strex  132  -gsivnissaaglmglaltagygaskwgvrgltkigavewgta--rvxvn
Seq ID No 1 134  -gvivnagsihsfvslptptayssakggvklitqnlctayakyg--irin
Seq ID No 2 135  tgsiinisgiegivadpklasynaskggvrifsksaalhcaqagyrirvn
Seq ID No 3 137  -gaivnmasilgsvgfanacayvsakhallgltktaameyaaqg--vrin
Seq ID No 4 150  -gsivnvasilgsvgfagspayvsakhgvvgltkagaaeyaarg--irin
Seq ID No 5 140  -gaivnmasilghvgmpgaasynaskggvvnltrslgvshaqdg--irvn
Seq ID No 6 138  -gvivnmasilgtvgfasspayvaakhavvgltkaaakdygrqg--lrin
Seq ID No 7 136  -gaivnmasilgsvgfngagayvsakhavvgmtknaaleyaqkg--irvn 2bhd_Strex  179  svhpgmtyggmtaavgiergegkypnt-----tpmgxvgeadedagavvf
Seq ID No 1 181  avcpgyidtplgsv-n-----pqqkeylaslhpqgrlgtpeevakavlf
Seq ID No 2 185  tihpgyiwtpmvegyltslgdveggrqviskmhpigrmgepddiaygvly
Seq ID No 3 184  avgpafidtplsknld-----dqvlgqlaglhpigrlgtpeevsaltcf
Seq ID No 4 197  avgpgfidtpll-ktmd-----eaaykglvalhpagrlgrseevaeliaf
Seq ID No 5 187  avcpgfvatpliera-t-----eeararlvaahpigrlghadevakavlf
Seq ID No 6 185  svgpgfikthpldggld-----dqtqtylsglhavfrmgesaevaalvaf
Seq ID No 7 183  svgpafidtplldq-ld-----sdtrqalvgrhpigrlgradevaglvvf 2bhd_Strex  223  ilsdaasyvtgaelavdggwttgptvayvmgq
Seq ID No 1 225  lasddasfvngttllvdggytar---------
Seq ID No 2 235  lgsdesnfmtgselvidggytaq---------
Seq ID No 3 229  ilsgrasfitgsyhlvdggyttr---------
Seq ID No 4 241  ilsdrasfvagsyhlvdgaytav---------
Seq ID No 5 231  lasddasfivgtslmvdggycaq---------
Seq ID No 6 230  lcsaeasfltggyylvdggytaq---------
Seq ID No 7 227  ilsdrasfitgsyhlvdggytal---------
```

Multi-way amino acid sequence comparison of selected proteins. Scoring matrix BLOSUM 62. Illustrated in shaded form: positionally specific identical amino acid moieties, compared to a reference sequence of 3alpha,20beta-hydroxysteroid dehydrogenase from *Streptomyces hydrogenans*, Accession Code 2bhd_Strex. The sequence motifs claimed by the inventors are framed.

Surprisingly, it has been possible to show for all seven sequences that they are NADH-dependent R-ADHs which possess sufficient stability, in particular against 2-propanol. Furthermore, it has been possible to show for all seven enzymes that they are suitable for enzymatic reduction processes with a cosubstrate-coupled coenzyme regeneration.

This is a surprising and unexpected result, particularly since the sequences exhibit a distinctly low degree of homology among each other (Table 2) and, even in sequence comparisons (Pubmed/Blast), no related sequences could be identified which would have given a functional hint in this direction (Table 1).

On the other hand, it has in turn been possible to show that the present enzymes differ sufficiently in their enzymatic properties and complement each other with regard to their process suitability, in particular with specific targets.

Thus, the use of the aforesaid oxidoreductases in the process according to the invention represents no equivalent alternative to the established prior art, but a broadening of the existing spectrum.

TABLE 2

Two-by-two amino acid sequence comparison of selected oxidoreductases

| SEQ ID NO | Organism | SEQ ID NO: 1 Bacillus cereus ATCC 14579 | SEQ ID NO: 2 Methylibium petroleiphilum Pm1 | SEQ ID NO: 3 Mesorhizobium sp. | SEQ ID NO: 4 Streptomyces coelicolor | SEQ ID NO: 5 Ralstonia | SEO ID NO: 6 Herpentosiphon aurantiacus | SEQ ID NO: 7 Paracoccus denitrificans |
|---|---|---|---|---|---|---|---|---|
| SEQ ID NO: 1 | Bacillus cereus ATCC 14579 | 100 | 37/5 | 41/2 | 40/6 | 54/2 | 41/3 | 38/2 |
| SEQ ID NO: 2 | Methylibium petroleiphilum Pm1 | 37/5 | 100 | 37/6 | 33/8 | 41/5 | 39/4 | 43/4 |
| SEQ ID NO: 3 | Mesorhizobium sp. | 41/2 | 37/6 | 100 | 56/6 | 41/2 | 56/0 | 64/0 |
| SEQ ID NO: 4 | Streptomyces coelicolor | 40/6 | 33/8 | 56/6 | 100 | 43/3 | 53/5 | 54/5 |
| SEQ ID NO: 5 | Ralstonia | 54/2 | 41/5 | 41/2 | 43/3 | 100 | 45/1 | 46/4 |
| SEO ID NO: 6 | Herpentosiphon aurantiacus | 41/3 | 39/4 | 56/0 | 53/5 | 45/1 | 100 | 53/1 |
| SEQ ID NO: 7 | Paracoccus denitrificans | 38/2 | 43/4 | 64/0 | 54/5 | 46/4 | 53/1 | 100 |

The degree of homology in Table 2 is indicated as percent of identical amino acid moieties and as the number of shifts in an optimum pairwise alignment. The optimum alignment is thereby determined by means of the BLAST-algorithm (Basic Local Alignement Search Tool) (Altschul et al. 1990, Proc. Natl. Acd. Sci. USA. 87: 2264-2268).

As a basis, the PAM30 matrix is used as a scoring matrix for evaluating the sequence similarity (Dayhoff; M. O., Schwarz, R. M., Orcutt, B. C. 1978. "A model of evolutionary change in Proteins" in "Atlas of Protein Sequence and structure" 5(3) M. O. Dayhoff (ed) 345-352, National Biomedical Research foundation).

It is the object of the invention to provide a process for the enantioselective enzymatic reduction of keto compounds to the corresponding chiral hydroxy compounds which covers a broad substrate spectrum and yields high turnovers under process technological conditions.

According to the invention, said object is achieved by a process of the initially mentioned kind which is characterized in that, for reducing the keto compounds, a polypeptide is used which exhibits an R-ADH-signature H-[P; A]-[I; A; Q; V; L]-[G; K]-R at positions 204-208 and the following further structural features in their entirety:

(i) an N-terminal Rossmann-Fold GxxxGxG,
(ii) an NAG-motif at position 87,
(iii) a catalytic triad consisting of S 139, Y 152 and K 156,
(iv) a negatively charged amino acid moiety at position 37,
(v) two C-terminal motifs in the dimerization domain [A; S]-S-F and [V; I]-DG-[G; A]-Y-[T; C; L]-[A; T; S]-[Q; V; R; L; P],
(vi) Val or Leu at position 159 (4 positions downstream of K 156),
(vii) Asn at position 178, and
(viii) a proline moiety at position 188.

According to a preferred embodiment of the process according to the invention, a polypeptide is used for reducing the keto compounds (a) which comprises one of the amino acid sequences SEQ ID NO:1 to SEQ ID NO:7, or
(b) in which at least 70% of the amino acids are identical to the amino acids of one of the amino acid sequences SEQ ID NO:1 to SEQ ID NO:7, or
(c) for which a nucleic acid sequence from the group consisting of SEQ ID NO:8 to SEQ ID NO:14 encodes, or
(d) for which a nucleic acid sequence encodes which hybridizes to one of the nucleic acid sequences mentioned in (c) under stringent conditions.

By a nucleic acid sequence which hybridizes, for example, to SEQ ID NO:14 under stringent conditions, a polynucleotide is understood which can be identified via the colony hybridization method, the plaque hybridization method, the Southern hybridization method or comparable methods, using SEQ ID NO:14 or partial sequences of SEQ ID NO:14 as a DNA probe. For this purpose, the polynucleotide immobilized on a filter is hybridized, for example, to SEQ ID NO:14 in a 0.7-1 M NaCl solution at 65° C. Hybridization is carried out as described, for instance, in Protocol 32 of Molecular Cloning, A Laboratory Manual, Second Edition (Cold Spring Harbor Laboratory Press, 1989) or in similar publications. Subsequently, the filter is washed with a 0.1 to 2-fold SSC solution at 65° C., wherein a 1-fold SSC solution is understood to be a mixture consisting of 150 mM NaCl and 15 mM sodium citrate.

A polynucleotide which hybridizes to the polynucleotide SEQ ID NO:8, SEQ ID NO:9, SEQ ID NO:10, SEQ ID NO:11, SEQ ID NO:12, SEQ ID NO:13 or SEQ ID NO:14 under the above-mentioned stringent conditions should exhibit at least 68% sequence identity to the polynucleotide sequence SEQ ID NO:8, SEQ ID NO:9, SEQ ID NO:10, SEQ ID NO:11, SEQ ID NO:12, SEQ ID NO:13 or SEQ ID NO:14, respectively, better an identity of at least 80%, even better an identity of 95%.

According to a further preferred embodiment, keto compounds of general formula I are used,

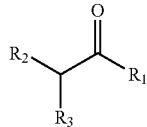

(I)

wherein $R_1$, $R_2$ and $R_3$ independently of each other are selected from the group consisting of
1) —H, provided that $R_1$ is not H,
2) —($C_1$-$C_{20}$)-alkyl, wherein alkyl is linear-chain or branched,
3) —($C_2$-$C_{20}$)-alkenyl, wherein alkenyl is linear-chain or branched and optionally contains up to four double bonds,
4) —($C_2$-$C_{20}$)-alkynyl, wherein alkynyl is linear-chain or branched and optionally contains up to four triple bonds,
5) —($C_6$-$C_{24}$)-aryl,
6) —($C_1$-$C_8$)-alkyl-($C_6$-$C_{14}$)-Aryl,
7) —($C_5$-$C_{14}$)-heterocycle,
8) —($C_3$-$C_7$)-cycloalkyl,
wherein the moieties mentioned above under 2) to 8) are unsubstituted or substituted one, two or three times, independently of each other, by —OH, halogen, —$NO_2$, —$NH_2$, —NHP and/or -M, wherein P stands for —($C_1$-$C_7$)-alkyl, —($C_2$-$C_7$)-alkenyl, —($C_2$-$C_7$)-alkynyl, —($C_6$-$C_{14}$)-aryl or a protective group selected from benzyloxy carbonyl, triphenyl methyl and t-butyl carbonyl, and M stands for —($C_1$-$C_7$)-alkyl, —($C_2$-$C_7$)-alkenyl, —($C_2$-$C_7$)-alkynyl, —($C_6$-$C_{14}$)-aryl or —($C_1$-$C_8$)-alkyl-($C_6$-$C_{14}$)-aryl, wherein —($C_6$-$C_{14}$)-aryl in —($C_1$-$C_8$)-alkyl-($C_6$-$C_{14}$)-aryl is unsubstituted or substituted one, two or three times by halogen, and
9) —$CH_2$—X—R, wherein X stands for O or S and R is selected from —($C_1$-$C_7$)-alkyl, phenyl and benzyl, wherein phenyl and benzyl are substituted one, two or three times by —($C_1$-$C_7$)-alkyl, —S($C_1$-$C_3$)-alkyl, —O($C_1$-$C_3$)-alkyl, —$NO_2$, —$SCF_3$, halogen, —C(O)($C_1$-$C_3$)-alkyl and/or —CN,
or $R_1$ forms with $R_2$, $R_1$ with $R_3$ or $R_2$ with $R_3$, a ring comprising 3-6 C-atoms which is unsubstituted or substituted one, two or three times, independently of each other, by —OH, halogen, —$NO_2$, —$NH_2$, —NHP and/or -M, and the remaining moiety is selected from the moieties mentioned above under 1) to 9).

According to another preferred embodiment, diketones of general formula II

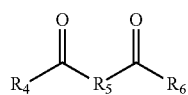

(II)

are used, wherein
$R_5$ stands for $(CH_2)_n$ with n=0-20, —($C_6$-$C_{14}$)-aryl or —($C_5$-$C_{14}$)-heterocycle,
$R_4$ and $R_6$, independently of each other, stand for —($C_1$-$C_{20}$)-alkyl or an ester group,
wherein $R_4$, $R_5$ and $R_6$ are unsubstituted or substituted one, two or three times, independently of each other, by —($C_1$-$C_4$)-alkyl, —OH, halogen, —$NO_2$ and/or —$NH_2$.

In the process according to the invention, it is furthermore preferred that
the oxidized cofactor NAD formed by the oxidoreductase/dehydrogenase is regenerated continuously, and
a secondary alcohol having the general formula $R_XR_Y$-CHOH is used for cofactor regeneration, wherein $R_X$ and $R_Y$, independently of each other, are a branched or unbranched $C_1$-$C_8$-alkyl group and $C_{total} \geq 3$.

The term "NAD" means nicotinamide adenine dinucleotide, the term "NADH" stands for reduced nicotinamide adenine dinucleotide.

The secondary alcohols (=cosubstrates) are converted to the corresponding ketones and NADH with the aid of the oxidoreductases used and NAD, whereby a regeneration of NADH occurs. In doing so, the portion of the cosubstrate for the regeneration ranges from 5 to 95% by volume, based on the total volume, preferably from 10 to 70%, particularly preferably from 20 to 50%.

Particularly preferably, 2-propanol or 2-butanol is used as a secondary alcohol for cofactor regeneration. Preferably, in case of 2-propanol, 10-70% (v/v), particularly preferably 20-50% (v/v), is used.

By the term "aryl", aromatic carbon moieties comprising 6 to 24 carbon atoms within the ring/in the (anellated and completely conjugated) rings are understood. —($C_6$-$C_{24}$)-Aryl moieties are, for instance, phenyl, naphthyl, e.g., 1-naphthyl, 2-naphthyl, biphenylyl, e.g., 2-biphenylyl, 3-biphenylyl and 4-biphenylyl, anthracyl, fluorenyl, phenantryl or cyclopentanoperhydrophenantryl. Biphenylyl moieties, naphthyl moieties and in particular phenyl moieties are preferred aryl moieties.

By the term "halogen", an element from the family of fluorine, chlorine, bromine or iodine is understood.

By the term "—($C_1$-$C_{20}$)-alkyl", a hydrocarbon moiety is understood the carbon chain of which is linear-chain or branched and comprises 1 to 20 carbon atoms, for example, methyl, ethyl, propyl, isopropyl, butyl, tertiary butyl, pentyl, hexyl, heptyl, octyl, nonyl, decanyl etc.

By the term "—($C_3$-$C_7$)-cycloalkyl", cyclic hydrocarbon moieties such as cyclopropyl, cyclobutyl, cyclopentyl, cyclohexyl or cycloheptyl are understood.

The term "—($C_5$-$C_{14}$)-heterocycle" stands for a monocyclic or bicyclic 5-membered to 14-membered heterocyclic ring which is partially or completely saturated. N, O and S are examples of heteroatoms. Moieties derived from pyrrole, furan, thiophene, imidazole, pyrazole, oxazole, isoxazole, thiazole, isothiazole, tetrazole, 1,2,3,5-oxathiadiazole-2-oxide, triazolone, oxadiazolone, isoxazolone, oxadiazolidinedione, triazole, which are substituted, e.g., by F, —CN, —$CF_3$ or —C(O)—O—($C_1$-$C_4$) alkyl, 3-hydroxypyrro-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, carboline and benzanellated, cyclopenta-, cyclohexa- or cyclohepta-anellated derivatives of said heterocycles are examples for the term "—($C_5$-$C_{14}$)-heterocycle". The moieties 2- or 3-pyrrolyl, phenyl pyrrolyl such as 4- or 5-phenyl-2-pyrrolyl, 2-furyl, 2-thienyl, 4-imidazolyl, methylimidazolyl, e.g., 1-methyl-2-, -4- or -5-imidazolyl, 1,3-thiazole-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g., 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, e.g., 2- or 3-(N-methylpyrrolidinyl), piperazinyl, morpholinyl, thiomorpholinyl, tetrahydrothienyl or benzodioxolanyl are particularly preferred.

Preferred compounds of Formula I are, for example, ethyl-4-chloroacetoacetate, methyl acetoacetate, ethyl-8-chloro-6-oxooctanoic acid, ethyl-3-oxovalerate, 4-hydroxy-2-butanone, ethyl-2-oxovalerate, ethyl-2-oxo-4-phenylbutyric acid, ethyl pyruvate, ethyl phenyl glyoxylate, 1-phenyl-2-propanone, 2-chloro-1-(3-chlorophenyl)ethane-1-one, acetophenone, 2-octanone, 3-octanone, 2-butanone, 1-[3,5-bis(trifluoromethyl)phenyl]ethane-1-one, 1,4-dichloro-2-butanone, acetoxyacetone, phenacyl chloride, ethyl-4-bromoacetoacetate, 1,1-dichloroacetone, 1,1,3-trichloroacetone or 1-chloroacetone.

Aromatic or heteroaromatic compounds of general formula R—CO—CH2—X are particularly preferred compounds, wherein X=halogen and R represents a moiety according to the above definition of Formula I.

Further preferred compounds are diketones such as 2,5-hexanedione, 2,4-pentanedione, 2,7-octanedione, 2,7-dimethyl-3,6-octanedione or diacetyl.

In the process according to the invention, the oxidoreductases can be used either in a completely purified or in a partially purified state or the process can be performed with cells containing the described oxidoreductases. In doing so, the cells used can be provided in a native, permeabilized or lysed state. Preferably, the cloned oxidoreductases according to SEQ ID NO:1, SEQ ID NO:2, SEQ ID NO:3, SEQ ID NO:4, SEQ ID NO:5, SEQ ID NO:6, SEQ ID NO:7 and homologues thereof, respectively, are used.

5.000 to 10 Mio U of oxidoreductase are used per kg of keto compound to be converted (no upper limit) The enzyme unit 1 U corresponds to the enzyme amount which is required for converting 1 mmol of the keto compound per minute (min).

In the process according to the invention, the keto compound is used in an amount ranging from 3% to 50%, based on the total volume, preferably ranging from 5% to 40%, in particular from 10% to 30%.

The TTN (total turn over number=mol of reduced keto compound/mol of cofactor used) achieved in the processes according to the invention normally ranges from $10^2$ to $10^5$, preferably, however, it is $\geq 10^3$.

For the regeneration of the cofactor, an alcohol dehydrogenase can additionally be added, preferably, however, the process is carried out only with an oxidoreductase (substrate-coupled coenzyme regeneration).

The aqueous portion of the reaction mixture in which the enzymatic reduction proceeds preferably contains a buffer, e.g., a potassium phosphate, tris/HCl or triethanolamine buffer, having a pH value of from 5 to 10, preferably a pH value of from 6 to 9. In addition, the buffer can contain ions for stabilizing or activating the enzymes, for example, zinc ions or magnesium ions.

While the process according to the invention is being carried out, the temperature suitably ranges from about 10° C. to 70° C., preferably from 20° C. to 45° C.

In a further possible embodiment of the process according to the invention, the enzymatic conversion is carried out in the presence of organic solvents which are not miscible with water or are miscible with water only to a limited degree and which are not involved in the cofactor regeneration, i.e., do not contain any oxidizable hydroxy groups. Said solvent can, for example, be a symmetric or unsymmetric di($C_1$-$C_6$)alkyl ether, a linear-chain or branched alkane or cycloalkane. Preferably, diethyl ether, tertiary butyl methyl ether, diisopropyl ether, dibutyl ether, ethyl acetate, butyl acetate, heptane, hexane, toluene, dichloromethane, cyclohexane or mixtures thereof is/are used as additional organic solvents.

The concentration of the cofactor NAD(H) in the aqueous phase generally ranges from 0.001 mM to 1 mM, in particular from 0.01 mM to 0.1 mM.

In the process according to the invention, a stabilizer of oxidoreductase/dehydrogenase can also be used. Suitable stabilizers are, for example, glycerol, sorbitol, 1,4-DL-dithiothreitol (DTT) or dimethyl sulfoxide (DMSO).

The enzymatic reduction itself proceeds under mild conditions so that the alcohols produced do not react any further. The process according to the invention has a long service life, an enantiomeric purity of normally more than 95% of the chiral alcohols produced and a high yield, based on the amount of keto compounds used.

The process according to the invention is carried out, for example, in a closed reaction vessel made of glass or metal. For this purpose, the components are transferred individually into the reaction vessel and stirred under an atmosphere of, e.g., nitrogen or air. The reaction time ranges from 1 hour to 48 hours, in particular from 2 hours to 24 hours.

Subsequently, the reaction mixture is reprocessed. For this purpose, the aqueous phase is separated, the organic phase is filtered. Optionally, the aqueous phase may be extracted once again and reprocessed further like the organic phase. Thereupon, the solvent is optionally evaporated from the filtered organic phase.

By way of the following examples, the invention is illustrated in further detail and the exceptional quality of the identified oxidoreductases is demonstrated in comparison to the prior art.

EXAMPLE 1

Cloning and Expression of Oxidoreductase SEQ ID NO:5

A) Cultivation of *Ralstonia eutropha* JMP134

Cells of *Ralstonia eutropha* DSM 4048 were cultivated in the following medium (pH 7.0) at 30° C. in a bacterial incubator: 0.5% peptone, 0.3% meat extract. On day 3 of the cultivation, cells were separated from the culture medium by centrifugation and stored at −80° C.

B) Amplification of the Gene Encoding for Selective Oxidoreductase

Genomic DNA was extracted according to the method described in "Molecular Cloning" by Manniatis & Sambrook (see above). The resulting nucleic acid served as a template for the polymerase chain reaction (PCR) involving specific primers which were derived from the gene sequence published under number 53760931 in the NCBI database. In doing so, the primers were provided in a 5'-terminal position with restriction sites for the endonucleases Nde I and Xho I, for subsequent cloning into an expression vector.

Amplification was carried out in a PCR buffer [10 mM tris-HCl, (pH 8.0); 50 mM KCl; 10 mM $MgSO_4$; 1 mM dNTP Mix; 20 pMol of each primer and 2.5 U of Platinum Pfx DNA polymerase (Invitrogen)] with 500 ng of genomic DNA and the following temperature cycles:

Cycle 1: 94° C., 2 min
Cycle 2×30: 94° C., 30 sec
  55° C., 30 sec
  68° C., 60 sec
Cycle 3: 68° C., 7 min
  4° C., ∞

The resulting PCR product having a size of about 750 bp was restricted after purification via a 1% agarose gel with the aid of the endonucleases Nde I and Xho I and was ligated into the backbone of the pET21a vector (Novagen), which backbone had been treated with the same endonucleases. After transforming 2 μl of the ligation batch into *E. coli* Top 10 F' cells (Invitrogen), plasmid DNAs of ampicillin-resistant colonies were tested for the presence of an insert having a size of 750 bp by using a restriction analysis with the endonucleases Nde I and Xho I. Plasmid preparations from the clones which were positive for the fragment were subjected to a sequence analysis and subsequently transformed into *Escherichia coli* BL21 Star (Invitrogen).

EXAMPLE 2

Expression of the Recombinant Oxidoreductases in *E. coli*

The *Escherichia coli* strains BL21 Star (Invitrogen, Karlsruhe, Germany) and RB791 (*E. coli* genetic stock, Yale, USA), respectively, which had been transformed with the expression construct, were cultivated in 200 ml LB medium (1% tryptone, 0.5% yeast extract, 1% NaCl) with ampicillin (50 μg/ml) or carbenicillin (50 μg/ml), respectively, until an optical density of 0.5, measured at 550 nm, was reached. The expression of recombinant protein was induced by adding isopropylthiogalactoside (IPTG) at a concentration of 0.1 mM. After 8 and 16 hours of induction, respectively, at 25° C. and 220 rpm, the cells were harvested and frozen at −20° C. For the activity test, 10 mg of cells were mixed with 500 μl of 100 mM TEA buffer pH 7.0 and 500 μl of glass beads and were digested for 10 mM using a globe mill. The lysate obtained was then used for the respective measurements in a diluted state. The activity test was composed as follows: 870 μl of 100 mM TEA buffer pH 7.0, 160 μg NAD(P)H, 10 μl diluted cell lysate. The reaction was started by adding 100 μl of a 100 mM substrate solution to the reaction mixture.

The oxidoreductases of the present invention could be expressed very efficiently in *Escherichia coli*. Table 3 shows the activities of the individual enzymes which were achieved in the expression.

TABLE 3

| | Expression vector | Expression strain | Reference | Activity U/g |
|---|---|---|---|---|
| SEQ ID NO: 1 | pET21a | BL21 Star | 2-octanone | 2650 U/g |
| SEQ ID NO: 2 | pET21a | BL21 Star | methyl acetoacetate | 1570 U/g |
| SEQ ID NO: 3 | pQE70 | BL21 Star | CLAEE | 3130 U/g |
| SEQ ID NO: 4 | pET21a | BL21 Star | ethyl-2-oxo-4-phenyl butanoate | 400 U/g |
| SEQ ID NO: 5 | pET21a | BL21 Star | CLAEE | 2890 U/g |
| SEQ ID NO: 6 | pQE70 | BL21 Star | methyl acetoacetate | 840 U/g |
| SEQ ID NO: 7 | pET21a | BL21 Star | methyl acetoacetate | 3295 U/g |

EXAMPLE 3

Characterization of the Recombinant Oxidoreductases SEQ ID NO:1-SEQ ID NO:7

3a: pH-Optimum

The buffers listed in Table 4 were produced. The concentration of the respective buffer components was in each case 50 mM.

TABLE 4

| pH-value | Buffer system |
|---|---|
| 4 | Na-acetate/acetic acid |
| 4.5 | Na-acetate/acetic acid |
| 5 | Na-acetate/acetic acid |
| 5.5 | $KH_2PO_4/K_2PO_4$ |
| 6 | $KH_2PO_4/K_2PO_4$ |
| 6.5 | $KH_2PO_4/K_2PO_4$ |
| 7 | $KH_2PO_4/K_2PO_4$ |
| 7.5 | $KH_2PO_4/K_2PO_4$ |
| 8 | $KH_2PO_4/K_2PO_4$ |
| 8.5 | $KH_2PO_4/K_2PO_4$ |
| 9 | glycine/NaOH |
| 9.5 | glycine/NaOH |
| 10 | glycine/NaOH |
| 11 | glycine/NaOH |

Measuring Batch (30° C.)-pH Optimum Reduction:

870 μl of each of the buffer systems mentioned in Table 3

20 μl of NADH 10 mM

10 μl of a diluted enzyme

After about 2 to 3 min of incubation,

100 μl of a substrate solution (100 mM) were added.

The respective reference substrate (Table 3) was used as a substrate for each oxidoreductase. The reaction was pursued for 1 min at 340 nm. In order to determine the pH-optimum, the enzymatic reaction in the respective buffer listed in Table 4 was determined. In order to determine the pH-optimum for the oxidation reaction, NAD was used as the cofactor and 2-propanol or 2-octanol was used as the substrate.

The results for the oxidoreductases SEQ ID NO:1-SEQ ID NO:7 are compiled in Table 5.

TABLE 5

| SEQ ID NO | pH-Opt. Red. | pH-Opt. Ox. |
|---|---|---|
| SEQ ID NO: 1 | 5.5-6.5 | 9.0-9.5 |
| SEQ ID NO: 2 | 5.0-5.5 | 9-10 |
| SEQ ID NO: 3 | 5.5 | 10-11 |
| SEQ ID NO: 4 | 5.5 | 9-10 |
| SEQ ID NO: 5 | 7.0-7.5 | 9.5-10 |
| SEQ ID NO: 6 | 5.5-6.5 | 7.5 |
| SEQ ID NO: 7 | 5.5 | 10-11 |

3b: pH Stability

The stability of the recombinant oxidoreductases was examined by storing them in the buffer systems mentioned in Table 4. For this purpose, the different buffers (50 mM) were prepared in the range from pH 4 to 11, and the oxidoreductases produced according to Example 4 were diluted therewith. After 30, 60 and 120 minutes of incubation, 10 μl were taken from the batch and used in the activity test according to Example 3a.

The initial value was thereby the measured value which was obtained immediately after the dilution (1:20) of the enzyme in a potassium phosphate buffer 50 mM pH=7.0. Under the given conditions, said value corresponded to an extinction change of approx. 0.70/min and was set as a 100% value. All subsequent measured values were put in relation to this value.

In Table 6, the pH ranges in which the enzymes exhibited no less than 50% of the initial activity with an incubation of 120 mM are compiled for the named oxidoreductases.

TABLE 6

| SEQ ID NO | pH-range stability |
|---|---|
| SEQ ID NO: 1 | 4.5-9.5 |
| SEQ ID NO: 2 | 7.0-10 |
| SEQ ID NO: 3 | 5.5-11 |
| SEQ ID NO: 4 | 5.5-9.5 |
| SEQ ID NO: 5 | 7.5-11 |
| SEQ ID NO: 6 | 6-11 |
| SEQ ID NO: 7 | 5-11 |

3c: Temperature Optimum

In order to determine the optimum test temperature, the enzyme activity for the oxidoreductases used according to the invention was measured in the standard measuring batch in a temperature range from 15° C. to 70° C.

The temperature optima determined are compiled in Table 7:

TABLE 7

| SEQ ID NO | $T_{opt}$ |
|---|---|
| SEQ ID NO: 1 | 55° C. |
| SEQ ID NO: 2 | 65° C. |
| SEQ ID NO: 3 | n.d |
| SEQ ID NO: 4 | n.d |
| SEQ ID NO: 5 | 45° C. |
| SEQ ID NO: 6 | 50° C. |
| SEQ ID NO: 7 | 45° C. |

3d: Temperature Stability

In an analogous manner as described under Example 3c, the temperature stability was determined for the range from 15° C. to 70° C. For this purpose, a dilution of the oxidoreductases used according to the invention was in each case incubated at the respective temperature for 60 min and 180 min and was subsequently measured at 30° C. with the abovementioned test batch. In Table 8, the temperature ranges in which the enzymes exhibited no less than 50% of the initial activity with an incubation of 120 min are compiled for the oxidoreductases.

TABLE 8

| SEQ ID NO | Temperature range |
|---|---|
| SEQ ID NO: 1 | 15-45° C. |
| SEQ ID NO: 2 | 15-35° C. |
| SEQ ID NO: 3 | n.d |
| SEQ ID NO: 4 | n.d |
| SEQ ID NO: 5 | 15-35° C. |
| SEQ ID NO: 6 | 15-35° C. |
| SEQ ID NO: 7 | 15-45° C. |

3e: Stability Against 2-propanol

The stability of the oxidoreductases to be examined against 2-propanol was tested by diluting the lysates obtained in Example 2 (from a recombinant expression) in a buffer (KPP 100 mM, pH=7.0) containing the corresponding percentage of 2-propanol (approx. 10 units/ml buffer). The batch was incubated at room temperature with constant thorough mixing (thermomixer at 170 rpm). After 24 h of incubation, 10 µl each were taken from the aqueous phase and used for the determination of the enzyme activity in the standard test batch (potassium phosphate buffer (KPP) 100 mM, pH=7.0, 0.2 mM NADH, 10 mM substrate). Also in this case, the initial value immediately after the dilution in the buffer was set to 100%, and all further values were put in relation thereto.

TABLE 9

Enzyme activity after 24 h of incubation with mixtures containing 2-propanol

| SEQ ID NO | Buffer | 10% 2-Propanol | 20% 2-Propanol | 30% 2-Propanol | 40% 2-Propanol |
|---|---|---|---|---|---|
| SEQ ID NO: 1 | 100% | 100% | 100% | 100% | 30% |
| SEQ ID NO: 2 | 100% | 100% | 100% | 100% | 30% |
| SEQ ID NO: 3 | 100% | 80-100% | 50-75% | 25-30% | 0% |
| SEQ ID NO: 4 | 100% | 80-100% | 50-75% | 0% | 0% |
| SEQ ID NO: 5 | 100% | 100% | 100% | 100% | 0% |
| SEQ ID NO: 6 | 100% | 80-100% | 50-75% | 50-75% | 50-75% |
| SEQ ID NO: 7 | 100% | 80-100% | 50-75% | 25-30% | 25-30% |

As can be seen from Table 9, all examined sequences exhibit an astounding stability in 2-propanol, i.e., all oxidoreductases are stable for at least 24 h in 20% isopropanol, but most enzymes still display substantial residual activities of up to 75% even after 24 h at 40% (v/v).

This shows that the sequences SEQ ID NO:1-SEQ ID NO:7 are particularly suitable for use in a substrate-coupled process with 2-propanol.

3f: Comparison of the Substrate Spectra of Oxidoreductases SEQ ID NO:1-SEQ ID NO:7

The substrate spectrum of the sequences to be characterized was determined by measuring the enzyme activity for reduction and oxidation with a number of ketones and alcohols. For this purpose, the standard measuring batch according to Example 2 was used with different substrates.

The activity with methyl acetoacetate was set to 100% for all enzymes, and all other substrates were put in relation thereto.

TABLE 10

Substrate spectra/reduction

| Substrate | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 |
|---|---|---|---|---|---|---|---|
| 1-Phenyl-2-propanone | 15% | 7% | 70% | 37% | <1% | <1% | 16% |
| Phenacyl chloride | 3.4% | 1% | 50% | <1% | <1% | 15% | 10% |
| Acetophenone | 3.5% | 6% | 30% | <1% | <1% | 3.5% | 32% |
| Acetonaphthone | 3% | 9% | 30% | 7% | <1% | 25% | 17% |
| Butyrophenone | 3% | 1% | <% | <1% | <1% | <1% | <1% |
| 2-Octanone | 92% | 2% | 33% | 70% | 26% | 23% | 49% |
| 3-Octanone | 22% | 2% | 15% | 5% | 13% | 2% | 15% |
| 2-Butanone | 8.5% | 4.5% | 30% | 5% | <1% | 7% | 6% |

TABLE 8-continued

| SEQ ID NO | Temperature range |
|---|---|
| SEQ ID NO: 6 | 15-35° C. |
| SEQ ID NO: 7 | 15-45° C. |

TABLE 10-continued

Substrate spectra/reduction

| Substrate | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 |
|---|---|---|---|---|---|---|---|
| Ethyl-2-oxovalerate | 3% | 60% | 70% | 17% | <1% | 15% | <1% |
| Ethyl-2-oxo-4-phenyl butyric acid | 3% | 50% | 118% | 35% | 45% | 18% | 10% |
| Ethyl pyruvate | 140% | 70% | 100% | 64% | 13% | 116% | 160% |
| Ethyl phenyl glyoxylate | 4.8% | 53% | 7.5% | 3% | <1% | <1% | <1% |
| Ethyl-4-chloroacetoacetate | 12.5% | 20% | 21% | 100% | 50% | 10% | <1% |
| Methyl acetoacetate | 100% | 100% | 100% | 100% | 100% | 100% | 100% |
| Ethyl-3-oxovalerate | 3.5% | 30% | 76% | 11% | <1% | 10% | 12% |
| Acetone | 4.5% | 16% | 38% | 5% | <1% | 3.5% | 8% |

The enantiomeric excesses were determined for selected substrates. The following reaction batch was used for this:

160 µl buffer
100 µl NAD (0.4 mg/ml)
20-50 µl 2-propanol
50 µl enzyme solution
2 mg substrate
Reaction conditions: 28° C., 24 h Upon completion of the incubation period, the samples were extracted with solvents depending on the substrate and were centrifuged. One aliquot was withdrawn, optionally, the extractant was removed completely, subsequently, the sample was dissolved in a suitable solvent, and the enantiomeric excess was determined by GC.

TABLE 11

Enantioselectivity for selected substrates

| Substrate | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 |
|---|---|---|---|---|---|---|---|
| Phenacyl chloride | ≥99.9% S | ≥99.9% S | ≥99.9% S | 97.5% S | 60-80% S | ≥99.9% S | ≥99.9% S |
| Acetophenone | 99.0% R | 98.5% R | 99.0% R | | | 99.0% R | 98.5% R |
| 2-Pentanone | ≥99.9% R | 98% R | 98% R | 95% R | 99.0% R | 97% R | 99.5% R |
| 2-Octanone | ≥99.9% R | ≥99.9% R | ≥99.9% R | ≥99.9% R | ≥99.9% R | ≥99.9% R | ≥99.9% R |
| 2-Butanone | ≥96.0% R | n.d | n.d | n.d | n.d | rac | 50% R |
| Ethyl pyruvate | 98.0% R | ≥99.9% R | ≥99.9% R | ≥99.9% R | ≥99.9% R | ≥99.9% R | ≥99.9% R |
| Ethyl-4-chloroacetoacetate | 99.0% S | ≥99.9% S | ≥99.9% S | ≥99.9% S | ≥99.9% S | ≥99.9% S | ≥99.9% S |
| Methyl acetoacetate | ≥99.9% R | ≥99.9% R | ≥99.9% R | 98.5% R | ≥99.9% R | ≥99.9% R | ≥99.9% R |

"rac": unselective reduction, i.e., both enantiomers form at a roughly identical ratio
n.d = not determined, no conversion
The enantiomeric excess is calculated as follows: ee(%) = ((R-alcohol − S-alcohol)/(R-alcohol + S-alcohol)) × 100.

The potential of the above-described oxidoreductases toward oxidation and hence the suitability for regeneration were compared by employing the following activity test: 870 µl of 100 mM TEA buffer, pH 8.0, 160 µg NAD, 10 µl diluted cell lysate. The reaction was started by adding 100 µl of a 100 mM substrate solution to the reaction mixture.

In this case, the substrate with the highest activity was set to 100%.

TABLE 12

Substrate spectra/oxidation

| Substrate | SEQ ID NO: 1 | SEQ ID NO: 2 | SEQ ID NO: 3 | SEQ ID NO: 4 | SEQ ID NO: 5 | SEQ ID NO: 6* | SEQ ID NO: 7 |
|---|---|---|---|---|---|---|---|
| S-2-Octanol | 0% | 0% | 0% | 0% | 0% | 0% | 0% |
| R-2-Octanol | 100% | 31% | 100% | 100% | 100% | 100% | 100% |
| S-2-Butanol | 1% | 20% | 30% | 2% | 2.5% | <2% | 0% |
| R-2-Butanol | 3% | 100% | 58% | 18% | 14% | 60% | 50% |
| S-Phenyl-2-propanol | 0% | 0% | 0% | 0% | 0% | 0% | 0% |
| R-Phenyl-2-propanol | <1% | 20% | 50% | 2% | 25% | 0% | 50% |

TABLE 12-continued

Substrate spectra/oxidation

| Substrate | SEQ ID NO: 1 | SEQ ID NO: 2 | SEQ ID NO: 3 | SEQ ID NO: 4 | SEQ ID NO: 5 | SEQ ID NO: 6* | SEQ ID NO: 7 |
|---|---|---|---|---|---|---|---|
| 2-Methyl-4-pentanol | <1% | 20% | 10% | 1% | 2.5% | 0% | 0% |
| 2-Propanol | 1.6% | 20% | 100% | 7% | 7% | 60% | 20% |
| Cyclohexanol | 0% | 20% | 0% | 0% | 0% | 0% | 0% |

*Oxidation hardly detectable

As can be seen from Tables 10-12, all seven sequences are clearly R-specific oxidoreductases. However, the examined enzymes differ clearly in the spectrum of preferred substrates as well as in the oxidation behaviour. Differences arise with regard to the preference for short-chain, rather low-molecular substrates over long-chain carbonyl compounds, similarly, different aromatic systems or also different substituents (such as halogen) are tolerated to a different degree.

Although a variety of enzymes are thus available which, in principle, indeed catalyze similar reactions, it was found out that both enzymes which catalyze the target reaction extremely efficiently and enzymes which do not catalyze the target reaction at all can be found among those individual substrates.

Furthermore, differences in enantioselectivity are also observed which indeed appear minor at first sight, but can be absolutely decisive for the applicability of individual enzymes for specific reduction processes given a specification of ee>99.0-99.9%, which today is common for pharmaceutical applications.

Also, the oxidative properties and hence the applicability in different processes with a substrate-coupled coenzyme regeneration vary between the examined enzymes as well as in comparison to the prior art.

Thus, the use of the named oxidoreductases in the process according to the invention does not represent an equivalent alternative to the established prior art, but a broadening of the existing spectrum.

EXAMPLE 4

Comparison of Oxidoreductases SEQ ID NO:1-SEQ ID NO:7 in Specific Processes

On the basis of the examples listed below, it shall now be shown for a few specific processes that the enzymes SEQ ID NO:1 to 7 can provide special solutions to concrete questions which also clearly exceed the existing prior art.

4.a Reduction of 3,6-octanedione to R,R-3,6-octanediol

For the purpose of screening for suitable enzymes for the development of a process with a substrate-coupled coenzyme regeneration for reducing 3,6-octanedione to R,R-3,6-octanediol, all enzymes were examined in the following reaction batch:

450 µl buffer, pH=7.0
0.05 mg NAD
50 µl 2-propanol
10 mg 3,6-octanedione

After 24 h of incubation at 25° C., the samples were extracted by means of dichloromethane and analyzed by GC.

In Table 13, the conversions and reaction products obtained are indicated.

TABLE 13

| SEQ ID NO | 3,6-Octanedione | Product (S) reduced once | Product (R) reduced once | S,S-3,6-Octanediol | R,R-3,6-Octanediol |
|---|---|---|---|---|---|
| SEQ ID NO: 1 | 95% | 0% | 5% | 0% | 0% |
| SEQ ID NO: 2 | 3% | 0% | 17% | 0% | 80% |
| SEQ ID NO: 3 | 10% | 0% | 45% | 0% | 45% |
| SEQ ID NO: 4 | 76% | 0% | 24% | 0% | 0% |
| SEQ ID NO: 5 | 95% | 0% | 5% | 0% | 0% |
| SEQ ID NO: 6 | 24% | 0% | 59% | 0% | 17% |
| SEQ ID NO: 7 | 43% | 0 | 47% | 0 | 10% |
| WO 2007/012428 Pichia farinosa | 85% | 0% | 15% | 0% | 0% |
| WO 2007/012428 Candida nemodendra | 95% | 0% | 5% | 0% | 0% |
| EP 1179 595 A1 Pichia finlandica | 3% | 0% | 17% | 0% | 80% |
| WO 2004/027055 Devosia | 40% | 0% | 50% | 0% | 10% |

As can be seen from Table 13, among the available enzymes, such can be found which, under the above-mentioned reaction conditions, are very well capable of reducing 3,6-octanedione to the desired R,R-octanediol (SEQ ID NO:2, SEQ ID NO:3 and P. finlandica), such which practically do not accept the substrate at all (SEQ ID NO:1, SEQ ID NO:5 and C. nemodendra) as well as such which would have to be used preferably if it was intended to produce the compound reduced once (SEQ ID NO:4).

4.b Reduction of 2,7-dimethyl-3,6-octanedione to (S,S)-2,7-dimethyl octane-3,6-diol For the purpose of screening for suitable enzymes for a process with a substrate-coupled coenzyme regeneration for reducing 2,7-dimethyl-3,6-octanedione to (S,S)-2,7-dimethyl octane-3,6-diol, the enzymes were examined in the following reaction batch:

450 µl buffer, pH=7.0
0.05 mg NAD
50 µl 2-propanol
10 mg 2,7-dimethyl-3,6-octanedione After 24 h of incubation at 25° C., the samples were extracted by means of dichloromethane and analyzed by GC.

In Table 14, the conversions and reaction products obtained are indicated.

TABLE 14

| SEQ ID NO | 2,7-Dimethyl-3,6-octanedione | Meso | (S,S)-2,7-Dimethyl octane-3,6-diol | (R,R)-2,7-Dimethyl-3,6-octanediol |
|---|---|---|---|---|
| SEQ ID NO: 1 | 100% | 0% | 0% | 0% |
| SEQ ID NO: 2 | 23% | 0 | 77% | 0% |
| SEQ ID NO: 3 | 100% | 0% | 0% | 0% |
| SEQ ID NO: 4 | 100% | 0% | 0% | 0% |
| SEQ ID NO: 5 | 100% | 0% | 0% | 0% |
| SEQ ID NO: 6 | 100% | 0% | 0% | 0% |
| SEQ ID NO: 7 | 100% | 0% | 0% | 0% |
| WO 2007/012428 Pichia farinosa | 100% | 0% | 0% | 0% |
| WO 2007/012428 Candida nemodendra | 100% | 0% | 0% | 0% |
| EP 1179 595 A1 Pichia finlandica | 100% | 0% | 0% | 0% |
| WO 2004/027055 Devosia | 100% | 0% | 0% | 0% |

As can be seen from Table 14, SEQ ID NO:2 provides a solution to this specific question, by contrast, no enzyme from the prior art is capable of catalyzing the desired reaction.

4.c Reduction of 2,4-pentanedione to R,R-2,4-pentanediol

For the purpose of screening for suitable enzymes for a process with a substrate-coupled coenzyme regeneration for reducing 2,4-pentanedione to R,R-2,4-pentanediol, the enzymes were examined in the following reaction batch:
450 µl buffer, pH=7.0
0.05 mg NAD
50 µl 2-propanol
10 mg 2,4-pentanedione After 24 h of incubation at 25° C., the samples were extracted by means of dichloromethane and analyzed by GC.

In Table 15, the conversions and reaction products obtained are indicated.

TABLE 15

| SEQ ID NO | 2,4-Pentanedione | Compound (R) reduced once | (S,S)-2,4-Pentanediol | (R,R)-2,4-Pentanediol |
|---|---|---|---|---|
| SEQ ID NO: 1 | 0% | 70% | 0% | 30% |
| SEQ ID NO: 2 | 0% | 19% | 0% | 81% |
| SEQ ID NO: 3 | 2% | 95% | 0% | 3% |
| SEQ ID NO: 4 | 6% | 93% | 0% | 1% |
| SEQ ID NO: 5 | 60% | 40% | 0% | 0% |
| SEQ ID NO: 6 | 100% | 0% | 0% | 0% |
| SEQ ID NO: 7 | 7% | 91% | 0% | 2% |
| WO 2007/012428 Pichia farinosa | 100% | 0% | 0% | 0% |
| WO 2007/012428 Candida nemodendra | 55% | 45% | 0% | 0% |
| EP 1179 595 A1 Pichia finlandica | 30% | 70% | 0% | 0% |
| WO 2004/027055 Devosia | 43% | 57% | 0% | 0% |

As can be seen from Table 15, the conversion of 2,4-pentanedione to R,R-2,4-pentanediol is possible with the oxidoreductases SEQ ID NO:1 and SEQ ID NO:2. Most enzymes convert this substrate only as far as to a mono-reduced compound. The prior art provides no solution to this, either.

On the other hand, for an efficient recovery of the mono-reduced compound, the oxidoreductases SEQ ID NO:3, SEQ ID NO:4 and SEQ ID NO:7 are even more recommendable than the prior art.

4.e Reduction of 1,1,1-trifluoroacetone to R-1,1,1-trifluoropropanol

For the purpose of screening for suitable enzymes for a process with a substrate-coupled coenzyme regeneration for reducing 1,1,1-trifluoroacetone to R-1,1,1-trifluoropropanol, the enzymes were examined in the reaction batch indicated below.

In doing so, the reaction batch accounts for the specific demand made on the reprocessing and conversion of this highly volatile substrate. In this case, a regeneration with isopropanol is not possible, in fact, the use of methyl pentanol is preferred in order to, on the one hand, prevent the volatile substrate (bp=22° C.) from escaping during the reaction and, on the other hand, enable the reprocessing of the reaction product R-1,1,1-trifluoropropanol (bp=80° C.). (The separation of 2-propanol would be impossible because of identical boiling points.)
450 µl buffer, pH=7.0
0.05 mg NAD
500 µl 2-methyl-4-pentanol
20 µl 1,1,1-trifluoroacetone After 24 h of incubation at 25° C., the samples were analyzed by GC.

In Table 16, the conversions and reaction products obtained are indicated.

TABLE 16

| SEQ ID NO | 1,1,1-Trifluoroacetone | R-1,1,1-Trifluoropropanol | S-1,1,1-Trifluoropropanol |
|---|---|---|---|
| SEQ ID NO: 1 | 0% | 99% | 1% |
| SEQ ID NO: 2 | 20% | 60% | 40% |
| SEQ ID NO: 3 | 2% | 70% | 30% |
| SEQ ID NO: 4 | 15% | 80% | 20% |
| SEQ ID NO: 5 | 50% | 85% | 15% |
| SEQ ID NO: 6 | n.d | n.d | n.d |
| SEQ ID NO: 7 | n.d | n.d | n.d |
| WO 2007/012428 Pichia farinosa | 0% | 97% | 3% |
| WO 2007/012428 Candida nemodendra | 50% | 99% | 1% |
| EP 1179 595 A1 Pichia finlandica | 50% | 99% | 1% |
| WO 2004/027055 Devosia | n.d | n.d | n.d |

As can be seen from Table 16, in this case, oxidoreductase SEQ ID NO:1 offers the best compromise between conversion and selectivity. Amazingly, most enzymes are not capable at all of reducing this substrate with a satisfactory enantioselectivity, whereby the diversity of the described enzymes despite a basically identical functionality is again emphasized.

4.f Reduction of 2-chloro-1-(3-hydroxyphenyl) ethane-1-one to (1S)-2-chloro-1-(3-hydroxyphenyl) ethane-1-ol For the purpose of screening for suitable enzymes for a process with a substrate-coupled coenzyme regeneration for reducing 2-chloro-1-(3-hydroxyphenyl)ethane-1-one to (1S)-2-chloro-1-(3-hydroxyphenyl)ethane-1-ol, the enzymes were examined in the following reaction batch:

400 μl buffer, pH=7.0
0.02 mg NAD
100 μl 2-propanol
25 mg 2-chloro-1-(3-hydroxyphenyl)ethane-1-one After 24 h of incubation at 25° C., the samples were extracted and analyzed by GC.

In Table 17, the conversions and reaction products obtained are indicated.

TABLE 17

| SEQ ID NO | 2-Chloro-1-(3-hydroxyphenyl)ethane1-one | (1R)-2-Chloro-1-(3-hydroxyphenyl)ethane-1-ol | (1S)-2-Chloro-1-(3-hydroxyphenyl)ethane-1-ol |
|---|---|---|---|
| SEQ ID NO: 1 | 100% | n.d | n.d |
| SEQ ID NO: 2 | 55% | 0% | 45% |
| SEQ ID NO: 3 | 40% | 0% | 60% |
| SEQ ID NO: 4 | 99% | n.d | n.d |
| SEQ ID NO: 5 | 100% | n.d | n.d |
| SEQ ID NO: 6 | 25% | 0% | 75% |
| SEQ ID NO: 7 | 83% | 0% | 17% |
| WO 2007/012428 Pichia farinosa | 100% | n.d | n.d |
| WO 2007/012428 Candida nemodendra | 100% | n.d | n.d |
| EP 1179 595 A1 Pichia finlandica | 98% | n.d | n.d |
| WO 2004/027055 Devosia | 100% | n.d | n.d |

As can be seen from Table 17, the conversion of 2-chloro-1-(3-hydroxyphenyl)ethane-1-one to (1S)-2-chloro-1-(3-hydroxyphenyl)ethane-1-ol is basically possible with the oxidoreductases SEQ ID NO:2, SEQ ID NO:3, SEQ ID NO:6 and SEQ ID NO:7, with those enzymes converting the substrate absolutely selectively. No enzyme from the prior art is capable of reducing this specific substrate.

4.g Reduction of ethyl-4-chloroacetoacetate to (S)-ethyl-4-chloro-3-hydroxybutyrate In the following, the enzymes SEQ ID NO:1-7 to be examined are tested in the industrial process for the reduction of ethyl-4-chloroacetoacetate to (S)-ethyl-4-chloro-3-hydroxybutyrate and are compared to the prior art.

For this purpose, the substrate ethyl-4-chloroacetoacetate was used at a high concentration (200 g/l) according to the prior art (WO 2006/087235) and the efficiency of the enzymes in the process with a substrate-coupled regeneration with 2-propanol was compared.

600 μl buffer, pH=8.0
0.2 mg NAD
200 μl 2-propanol
200 μl ethyl-4-chloroacetoacetate
240 μl enzyme recombinant from E. coli (20-60 units)

After 24 h of incubation at 25° C., the samples were extracted and analyzed by GC.

In Table 18, the conversions and reaction products obtained are indicated.

TABLE 18

| SEQ ID NO | Ethyl-4-chloroacetoacetate | (S)-Ethyl-4-chloro-3-hydroxybutyrate | (R)-Ethyl-4-chloro-3-hydroxybutyrate |
|---|---|---|---|
| SEQ ID NO: 1 | 90% | 10% | 0% |
| SEQ ID NO: 2 | 0% | 100% | 0% |
| SEQ ID NO: 3 | 0% | 100% | 0% |

TABLE 18-continued

| SEQ ID NO | Ethyl-4-chloroacetoacetate | (S)-Ethyl-4-chloro-3-hydroxybutyrate | (R)-Ethyl-4-chloro-3-hydroxybutyrate |
|---|---|---|---|
| SEQ ID NO: 4 | 70% | 30% | 0% |
| SEQ ID NO: 5 | 85% | 15% | 0% |
| SEQ ID NO: 6 | 60% | 40% | 0% |
| SEQ ID NO: 7 | 75% | 25% | 0% |
| WO 2007/012428 *Pichia farinosa* | 100% | n.d | n.d |
| WO 2007/012428 *Candida nemodendra* | 100% | n.d | n.d |
| EP 1179 595 A1 *Pichia finlandica* | 80% | 20% | 0% |
| WO 2004/027055 *Devosia* | 75% | 25% | 0% |

As can be seen from Table 18, in particular the enzymes SEQ ID NO:2 and SEQ ID NO:3 provide NADH-dependent alternatives to the existing, usually NADPH-dependent processes, which alternatives are interesting for the reduction of ethyl-4-chloroacetoacetate to (S)-ethyl-4-chloro-3-hydroxybutyrate. In contrast, the enzymes from the prior art are unsuitable since they display only insufficient conversions or no conversions at all, respectively, under process conditions.

The invention claimed is:

1. A process for stereoselective enzymatic reduction of keto compounds to corresponding chiral hydroxy compounds, wherein the keto compounds are reduced with an enantioselective, NADH-specific oxidoreductase, the process comprising:
   reducing the keto compounds using a polypeptide which exhibits an R-ADH-signature H-[P; A]-[I; A; Q; V; L]-[G; K]-R at positions 205-209 and has the following further structural features in their entirety:
   (i) an N-terminal Rossmann-Fold GxxxGxG,
   (ii) an NAG-motif at position 87,
   (iii) a catalytic triad consisting of S 139, Y 152 and K 156,
   (iv) a negatively charged amino acid moiety at position 37,
   (v) two C-terminal motifs in the dimerization domain [A; S]-S-F and [V; I]-DG-[G; A]-Y-[T; C; L]-[A; T; S]-[Q; V; R; L; P],
   (vi) Val or Leu at position 159 (4 positions downstream of K 156),
   (vii) Asn at position 178, and
   (viii) a proline moiety at position 188,
   wherein the position of the R-ADH-signature H-[P; A]-[I; A; Q; V; L]-[G; K]-R and structural features (i) to (viii) refer to 2bhd_Strex by multi-way amino acid sequence comparison
   and wherein:
(a) the polypeptide comprises one of the amino acid sequences SEQ ID NO:1 to SEQ ID NO:7, or
(b) the polypeptide is encoded by a nucleic acid sequence from the group consisting of SEQ ID NO:8 to SEQ ID NO:14, or
(c) the polypeptide is encoded by a nucleic acid sequence which hybridizes to one of the nucleic acid sequences mentioned in (b) and has at least 80% sequence identity to one of the nucleic acid sequences mentioned in (b).

2. The process according to claim 1, wherein keto compounds of general formula I or II are used,

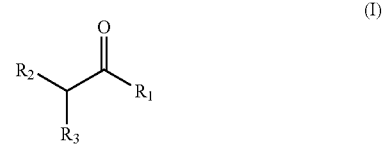

(I)

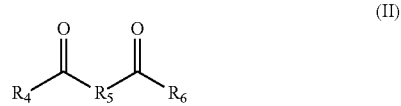

(II)

wherein $R_1$, $R_2$ and $R_3$ independently of each other are selected from the group consisting of:
1) —H, provided that $R_1$ is not H,
2) —$(C_1-C_{20})$-alkyl, wherein alkyl is linear-chain or branched,
3) —$(C_2-C_{20})$-alkenyl, wherein alkenyl is linear-chain or branched and optionally contains up to four double bonds,
4) —$(C_2-C_{20})$-alkynyl, wherein alkynyl is linear-chain or branched and optionally contains up to four triple bonds,
5) —$(C_6-C_{24})$-aryl,
6) —$(C_1-C_8)$-alkyl-$(C_6-C_{14})$-Aryl, 7) —($C_5$-$C_{14}$)-heterocycle,
8) —($C_3$-$C_7$)-cycloalkyl, wherein the moieties mentioned above under 2) to 8) are unsubstituted or substituted one, two or three times, independently of each other, by —OH, halogen, —$NO_2$, —$NH_2$, —NHP and/or -M, wherein P stands for —($C_1$-$C_7$)-alkyl, —($C_2$-$C_7$)-alkenyl, —($C_2$-$C_7$)-alkynyl, —($C_6$-$C_{14}$)-aryl or a protective group selected from benzyloxy carbonyl, triphenyl methyl and t-butyl carbonyl, and M stands for —($C_1$-$C_7$)-alkyl, —($C_2$-$C_7$)-alkenyl, —($C_2$-$C_7$)-alkynyl, —($C_6$-$C_{14}$)-aryl or —($C_1$-$C_8$)-alkyl-($C_6$-$C_{14}$)-aryl, wherein —($C_6$-$C_{14}$)-aryl in —($C_1$-$C_8$)-alkyl-($C_6$-$C_{14}$)-aryl is unsubstituted or substituted one, two or three times by halogen, and 9) —$CH_2$—X—R, wherein X stands for O or S and R is selected from —($C_1$-$C_7$)-alkyl, phenyl and benzyl, wherein phenyl and benzyl are substituted one, two or three times by —($C_1$-$C_7$)-alkyl, —S($C_1$-$C_3$)-alkyl, —O($C_1$-$C_3$)-alkyl, —$NO_2$, —$SCF_3$, halogen, —C(O) ($C_1$-$C_3$)-alkyl and/or —CN, or $R_1$ forms with $R_2$, $R_1$ with $R_3$ or $R_2$ with $R_3$, a ring comprising 3-6 C-atoms which is unsubstituted or substituted one, two or three times, independently of each other, by —OH, halogen, —$NO_2$, —$NH_2$, —NHP and/or -M, and the remaining moiety is selected from the moieties mentioned above under 1) to 9), and wherein $R_5$ stands for $(CH_2)_n$ with n=0-20, —($C_6$-$C_{14}$)-aryl or —($C_5$-$C_{14}$)-heterocycle, $R_4$ and $R_6$, independently of each other, stand for —($C_1$-$C_{20}$)-alkyl or an ester group, wherein $R_4$, $R_5$ and $R_6$ are unsubstituted or substituted one, two or three times, independently of each other, by —($C_1$-$C_4$)-alkyl, —OH, halogen, —$NO_2$ and/or —$NH_2$.

3. The process according to claim 1, wherein:

an oxidized cofactor NAD formed by the oxidoreductase/ dehydrogenase is regenerated continuously, and a secondary alcohol having the general formula $R_XR_Y$-CHOH is used for cofactor regeneration, wherein $R_X$ and $R_Y$, independently of each other, are a branched or unbranched $C_1$-$C_8$-alkyl group and $C_{total} \geq 3$.

4. The process according to claim 3, wherein an alcohol from the group consisting of 2-propanol, 2-butanol, 2-pentanol, 4-methyl-2-pentanol, 2-heptanol and 2-octanol, preferably 2-propanol, is used as a cosubstrate or a secondary alcohol, respectively.

5. The process according to claim 1, wherein the keto compound is used in an amount ranging from 3% to 50% based on the total volume.

6. The process according to claim 1, wherein TTN (total turn over number=mol of keto compound/mol of cofactor used) is $\geq 10^3$.

7. The process according to claim 1, wherein the process is carried out in an aqueous organic two-phase system.

8. The process according to claim 1, wherein, in addition, an organic solvent selected from diethyl ether, tertiary butyl methyl ether, diisopropyl ether, dibutyl ether, ethyl acetate, butyl acetate, heptane, hexane and cyclohexane is used.

* * * * *

SEQUENCE LISTING

<160> NUMBER OF SEQ ID NOS: 14

<210> SEQ ID NO 1
<211> LENGTH: 247
<212> TYPE: PRT
<213> ORGANISM: Bacillus cereus

<400> SEQUENCE: 1

Met Lys Leu Lys Asp Lys Val Ala Ile Ile Thr Gly Gly Ala Ser Gly
1               5                   10                  15

Ile Gly Glu Ser Thr Val Arg Leu Phe Ile Glu Glu Gly Ala Lys Val
            20                  25                  30

Val Ile Ala Asp Phe Ser Glu Arg Gly Lys Glu Leu Ser Asp Glu Leu
        35                  40                  45

Asn Ala His Gly Tyr Asn Thr Leu Phe Ile Lys Thr Asp Val Thr Lys
    50                  55                  60

Glu Ala Asp Ile Lys Gln Leu Ile His Glu Thr Val Ser Thr Tyr Gly
65                  70                  75                  80

Lys Leu Asp Ile Met Tyr Ala Asn Ala Gly Val Ala Asp Ala Pro
                85                  90                  95

Ala Asn Glu Leu Ser Tyr Glu Lys Trp Lys Arg Thr Ile Asp Ile Asn
            100                 105                 110

Leu Ser Gly Val Phe Leu Ser Asp Lys Tyr Ser Ile Glu Gln Phe Leu
        115                 120                 125

Lys Gln Gly Thr Gly Gly Val Ile Val Asn Ala Gly Ser Ile His Ser
    130                 135                 140

Phe Val Ser Leu Pro Thr Pro Thr Ala Tyr Ser Ser Ala Lys Gly Gly
145                 150                 155                 160

Val Lys Leu Leu Thr Gln Asn Leu Cys Thr Ala Tyr Ala Lys Tyr Gly
                165                 170                 175

Ile Arg Ile Asn Ala Val Cys Pro Gly Tyr Ile Asp Thr Pro Leu Leu
            180                 185                 190

Gly Ser Val Asn Pro Gln Gln Lys Glu Tyr Leu Ala Ser Leu His Pro
        195                 200                 205

Gln Gly Arg Leu Gly Thr Pro Glu Glu Val Ala Lys Ala Val Leu Phe
    210                 215                 220

Leu Ala Ser Asp Asp Ala Ser Phe Val Asn Gly Thr Thr Leu Leu Val

Asp Gly Gly Tyr Thr Ala Arg
            245

<210> SEQ ID NO 2
<211> LENGTH: 257
<212> TYPE: PRT
<213> ORGANISM: Methylibium petroleiphilum

<400> SEQUENCE: 2

Met Gly Arg Val Asp Asn Lys Val Ala Leu Val Thr Gly Gly Ala Lys
1               5                   10                  15

Gly Ile Gly Arg Ala Ser Ala Leu Met Leu Ala Arg Glu Gly Ala Arg
            20                  25                  30

Val Val Leu Thr Asp Val Glu Glu Ala Gln Gly Ser Ala Val Ala Lys
        35                  40                  45

Glu Ile Glu Arg Ala Gly Gly Lys Ala Leu Phe Leu Thr Gln Asp Val
    50                  55                  60

Thr Asp Glu Ser Arg Trp Val Glu Val Val Glu Lys Ala Arg Ala Gln
65                  70                  75                  80

Phe Gly Gly Leu Asn Ile Val Val Asn Asn Ala Gly Ile Gly Thr Ala
                85                  90                  95

Gly Ser Ala Glu Asp Glu Thr Leu Glu Ala Trp Arg Arg Leu Met Ser
            100                 105                 110

Val Asn Leu Asp Gly Val Phe Leu Gly Thr Lys His Ala Ile Arg Ala
        115                 120                 125

Met Lys Asn Gly Pro Gly Thr Gly Ser Ile Ile Asn Ile Ser Ser Ile
    130                 135                 140

Glu Gly Ile Val Ala Asp Pro Lys Leu Ala Ser Tyr Asn Ala Ser Lys
145                 150                 155                 160

Gly Gly Val Arg Ile Phe Ser Lys Ser Ala Ala Leu His Cys Ala Gln
                165                 170                 175

Ala Gly Tyr Arg Ile Arg Val Asn Thr Ile His Pro Gly Tyr Ile Trp
            180                 185                 190

Thr Pro Met Val Glu Gly Tyr Leu Thr Ser Leu Gly Asp Val Glu Gly
        195                 200                 205

Gly Arg Gln Val Ile Ser Lys Met His Pro Ile Gly Arg Met Gly Glu
    210                 215                 220

Pro Asp Asp Ile Ala Tyr Gly Val Leu Tyr Leu Gly Ser Asp Glu Ser
225                 230                 235                 240

Ser Phe Met Thr Gly Ser Glu Leu Val Ile Asp Gly Gly Tyr Thr Ala
                245                 250                 255

Gln

<210> SEQ ID NO 3
<211> LENGTH: 251
<212> TYPE: PRT
<213> ORGANISM: Mezorhizobium sp.

<400> SEQUENCE: 3

Met Thr Gly Glu Phe Lys Asp Lys Val Ala Leu Val Thr Gly Ala Gly
1               5                   10                  15

Ser Gly Ile Gly Ala Ala Ile Ala Arg Glu Leu Ala Thr Gly Gly Ala
            20                  25                  30

Glu Leu Val Val Ala Asp Leu Arg Glu Ser Ala Asn Arg Ile Val
        35                  40                  45

```
Glu Gly Ile Arg Ala Ser Gly Gly Arg Ala His Ala Phe Ala Val Asp
    50                  55                  60

Val Ala Asp Ala Glu Ala Val Glu Arg Met Val Asp Phe Ala Val Arg
65                  70                  75                  80

Thr Cys Gly Asp Leu His Leu Ala Val Asn Asn Ala Gly Ile Gly Gly
                85                  90                  95

Pro Ser Glu Pro Thr Ala Asp Tyr Pro Leu Asp Gly Trp Arg Lys Val
            100                 105                 110

Ile Asp Val Asn Leu Asn Gly Val Phe Tyr Gly Met Lys Tyr Glu Ile
        115                 120                 125

Ala Ala Ile Leu Lys Ser Gly Gly Ala Ile Val Asn Met Ala Ser
    130                 135                 140

Ile Leu Gly Ser Val Gly Phe Ala Asn Ala Cys Ala Tyr Val Ser Ala
145                 150                 155                 160

Lys His Ala Leu Leu Gly Leu Thr Lys Thr Ala Ala Met Glu Tyr Ala
                165                 170                 175

Ala Gln Gly Val Arg Ile Asn Ala Val Gly Pro Ala Phe Ile Asp Thr
            180                 185                 190

Pro Leu Leu Ser Lys Asn Leu Asp Asp Gln Val Leu Gly Gln Leu Ala
        195                 200                 205

Gly Leu His Pro Ile Gly Arg Leu Gly Thr Pro Glu Glu Val Ser Ala
    210                 215                 220

Leu Thr Cys Phe Leu Leu Ser Gly Arg Ala Ser Phe Ile Thr Gly Ser
225                 230                 235                 240

Tyr His Leu Val Asp Gly Gly Tyr Thr Thr Arg
                245                 250

<210> SEQ ID NO 4
<211> LENGTH: 263
<212> TYPE: PRT
<213> ORGANISM: Streptomyces coelicolor

<400> SEQUENCE: 4

Met Ser Thr Thr Gly Thr Thr Pro Ala Thr Gly Tyr Ala Ala Glu
1               5                   10                  15

Phe Ala Gly Arg Thr Ala Leu Val Thr Gly Ala Ala Ser Gly Ile Gly
                20                  25                  30

Leu Ala Thr Ala Arg Arg Leu Gly Ala Gly Gly Ala Arg Val Val Val
            35                  40                  45

Ala Asp Phe Asn Ala Glu Gly Ala Glu Lys Ala Ala Ala Glu Leu Arg
50                  55                  60

Ala Gly Gly Val Glu Ala Ala Val Glu Leu Asp Val Thr Arg Pro
65                  70                  75                  80

Glu Ser Val Glu Ala Ala Val Gly Phe Ala Val Asp Thr Phe Gly Ser
                85                  90                  95

Leu Asp Leu Ala Val Asn Asn Ala Gly Ile Gly Gly Pro Ser Ala Pro
            100                 105                 110

Thr Gly Glu Tyr Asp Val Ala Ala Tyr Gln Arg Val Val Arg Thr Asn
        115                 120                 125

Leu Asp Gly Val Phe Tyr Ser Met Arg Tyr Glu Leu Pro Ala Ile Glu
    130                 135                 140

Ala Ala Gly Lys Gly Gly Ser Ile Val Asn Val Ala Ser Ile Leu Gly
145                 150                 155                 160

Ser Val Gly Phe Ala Gly Ser Pro Ala Tyr Val Ala Ala Lys His Gly
```

-continued

```
                165                 170                 175
Val Val Gly Leu Thr Lys Ala Ala Ala Glu Tyr Ala Ala Arg Gly
            180                 185                 190

Ile Arg Ile Asn Ala Val Gly Pro Gly Phe Ile Asp Thr Pro Leu Leu
            195                 200                 205

Lys Thr Met Asp Glu Ala Ala Tyr Lys Gly Leu Val Ala Leu His Pro
        210                 215                 220

Ala Gly Arg Leu Gly Arg Ser Glu Glu Val Ala Glu Leu Ile Ala Phe
225                 230                 235                 240

Leu Leu Ser Asp Arg Ala Ser Phe Val Ala Gly Ser Tyr His Leu Val
                245                 250                 255

Asp Gly Ala Tyr Thr Ala Val
            260

<210> SEQ ID NO 5
<211> LENGTH: 253
<212> TYPE: PRT
<213> ORGANISM: Ralstonia eutropha

<400> SEQUENCE: 5

Met Glu Tyr Ile Asp Met Lys Leu Lys Asp Lys Val Ala Ile Val Thr
1               5                   10                  15

Gly Gly Ala Ser Gly Ile Gly Glu Ala Thr Val Arg Leu Phe Ala Ser
            20                  25                  30

Gln Gly Ala Ser Val Val Ile Ala Asp Arg Ser Ala Leu Gly Glu Lys
        35                  40                  45

Leu Ala Arg Glu Leu Ser Glu Ser Ser Leu Ala Ala His Tyr Ser Glu
    50                  55                  60

Val Asp Val Ser Arg Glu Asp Asp Thr Arg Arg Leu Ile Asp Asp Thr
65                  70                  75                  80

Val Ser Arg Phe Gly Arg Leu Asp Ile Met Val Ala Asn Ala Gly Ile
                85                  90                  95

Ala His Pro Ser Ala Pro Val Glu Asp Val Ser Val Glu Gln Trp Gln
            100                 105                 110

Gln Met Ile Asp Val Asn Leu Thr Gly Val Phe Leu Ser Asn Lys Leu
        115                 120                 125

Ala Ile Val Gln Met Lys Lys Gln Gly Thr Gly Gly Ala Ile Val Asn
    130                 135                 140

Met Ala Ser Ile Leu Gly His Val Gly Met Pro Gly Ala Ala Ser Tyr
145                 150                 155                 160

Asn Ala Ala Lys Gly Gly Val Val Asn Leu Thr Arg Ser Leu Gly Val
                165                 170                 175

Ser His Ala Gln Asp Gly Ile Arg Val Asn Ala Val Cys Pro Gly Phe
            180                 185                 190

Val Ala Thr Pro Leu Ile Glu Arg Ala Thr Glu Glu Ala Arg Ala Arg
        195                 200                 205

Leu Val Ala Ala His Pro Ile Gly Arg Leu Gly His Ala Asp Glu Val
    210                 215                 220

Ala Lys Ala Val Leu Phe Leu Ala Ser Asp Asp Ala Ser Phe Ile Val
225                 230                 235                 240

Gly Thr Ser Leu Met Val Asp Gly Gly Tyr Cys Ala Gln
                245                 250

<210> SEQ ID NO 6
<211> LENGTH: 252
```

<212> TYPE: PRT
<213> ORGANISM: Herpentosiphon aurantiacus

<400> SEQUENCE: 6

Met Asn Gln Tyr Asp Phe Arg Gly Lys Val Ala Leu Val Thr Gly Gly
1               5                   10                  15

Ala Ser Gly Ile Gly Ala Ala Cys Val His Thr Phe Ala Arg Gly Gly
                20                  25                  30

Ala Lys Val Ala Ile Val Asp Arg Asn Gln Asp Leu Gly Ala Gln Thr
            35                  40                  45

Val Ala Val Arg Glu Ala Gly Asp Ala Ile Phe Leu Pro Val
50                  55                  60

Asp Val Ala Gln Ser Gly Ala Val Glu Ala Met Val Thr Asp Thr Ile
65                  70                  75                  80

Thr Ala Phe Gly Gln Leu Asp Ile Ala Val Asn Asn Ala Gly Ile Gly
                85                  90                  95

Gly Glu Ser Asn Pro Thr Gly Thr Tyr Ser Ile Glu Gly Trp Gln Thr
                100                 105                 110

Val Ile Asp Val Asn Leu Asn Gly Val Phe Tyr Cys Met Arg Tyr Glu
            115                 120                 125

Ile Pro Ala Met Leu Ala Gln Gly Gly Val Ile Val Asn Met Ala
130                 135                 140

Ser Ile Leu Gly Thr Val Gly Phe Ala Ser Ser Pro Ala Tyr Val Ala
145                 150                 155                 160

Ala Lys His Ala Val Val Gly Leu Thr Lys Ala Ala Ala Leu Asp Tyr
                165                 170                 175

Gly Arg Gln Gly Leu Arg Ile Asn Ser Val Gly Pro Gly Phe Ile Lys
            180                 185                 190

Thr Pro Leu Leu Asp Gly Gly Leu Asp Asp Gln Thr Gln Thr Tyr Leu
                195                 200                 205

Ser Gly Leu His Ala Val Gly Arg Met Gly Glu Ser Ala Glu Val Ala
210                 215                 220

Ala Leu Val Ala Phe Leu Cys Ser Ala Glu Ala Ser Phe Leu Thr Gly
225                 230                 235                 240

Gly Tyr Tyr Leu Val Asp Gly Gly Tyr Thr Ala Gln
                245                 250

<210> SEQ ID NO 7
<211> LENGTH: 249
<212> TYPE: PRT
<213> ORGANISM: Paracoccus denitrificans

<400> SEQUENCE: 7

Met Asp Ile Arg Phe Asp Asn Lys Ile Ala Leu Val Thr Gly Ala Gly
1               5                   10                  15

Ser Gly Leu Gly Glu Ala Ile Ala Leu Glu Leu Ala Ala Ser Gly Ala
                20                  25                  30

Thr Val Val Ala Ala Asp Leu His Glu Ala Thr Ala Arg Ala Thr Ala
            35                  40                  45

Asp Arg Ile Val Ala Ala Gly Gly Lys Ala Lys Ala Val Ala Gly Asp
50                  55                  60

Val Ser Asp Pro Asp Ala Val Arg Lys Ala Val Glu Val Ala Lys Gly
65                  70                  75                  80

Leu Gly Gly Leu His Leu Leu Val Asn Asn Ala Gly Ile Gly Gly Pro
                85                  90                  95

```
Ser Ala Pro Val Gly Asp Tyr Pro Leu Asp Gly Trp Lys Lys Val Ile
            100                 105                 110
Asp Val Asn Leu Asn Ala Val Phe Tyr Gly Met Arg Tyr Gly Ile Pro
        115                 120                 125
Ala Met Leu Asp Ala Gly Gly Ala Ile Val Asn Met Ala Ser Ile
    130                 135                 140
Leu Gly Ser Val Gly Phe Asn Gly Ala Gly Tyr Val Ser Ala Lys
145                 150                 155                 160
His Ala Val Val Gly Met Thr Lys Asn Ala Ala Leu Glu Tyr Ala Gln
                165                 170                 175
Lys Gly Ile Arg Val Asn Ser Val Gly Pro Ala Phe Ile Asp Thr Pro
            180                 185                 190
Leu Leu Asp Gln Leu Asp Ser Asp Thr Arg Gln Ala Leu Val Gly Arg
        195                 200                 205
His Pro Ile Gly Arg Leu Gly Arg Ala Asp Glu Val Ala Gly Leu Val
    210                 215                 220
Val Phe Leu Leu Ser Asp Arg Ala Ser Phe Ile Thr Gly Ser Tyr His
225                 230                 235                 240
Leu Val Asp Gly Gly Tyr Thr Ala Leu
                245

<210> SEQ ID NO 8
<211> LENGTH: 744
<212> TYPE: DNA
<213> ORGANISM: Bacillus cereus

<400> SEQUENCE: 8
atgaaattaa aagacaaagt agcaatcata actggtggtg caagtggaat tggcgaatct    60
actgttcgtc tttttatcga agaaggtgca aaagtagtta ttgctgactt ttctgaacgt   120
ggaaaagaac tatcagatga attgaatgca catggatata atacgttatt tattaaaacc   180
gatgtaacaa aagaggcaga tattaaacag ctaattcatg agacagtaag tacatacggt   240
aaattagata ttatgtatgc caatgccggc gttgctgatg atgcaccggc aaacgaatta   300
tcctatgaaa gtggaaaag aactattgat attaatttgt ctggggtatt cctttctgat   360
aaatattcga ttgaacaatt tcttaaacaa ggtacaggtg gtgtcatcgt taacgctggt   420
tcgattcata gttttgtttc attacctaca ccaacagcat actcctctgc aaaaggtggt   480
gtgaaactat taactcaaaa tttatgtact gcctacgcta aatatggaat acgtattaac   540
gcggtgtgcc ctggttatat tgacaccccct ttactaggta gtgttaatcc tcaacagaaa   600
gaatatttag cttcacttca tccacaaggc agacttggaa caccagaaga agtcgctaaa   660
gctgtcttat ttttagcaag tgatgatgct agttttgtta acggcacaac acttcttgtt   720
gatggaggct atactgcacg ttaa                                          744

<210> SEQ ID NO 9
<211> LENGTH: 774
<212> TYPE: DNA
<213> ORGANISM: Methylibium petroleiphilum

<400> SEQUENCE: 9
atgggacgtg tggacaacaa ggtggcgctg gtgaccggtg gtgccaaggg catcggccgg    60
gccagcgcac tgatgctggc gcgcgaaggt gcccgcgtgg tgctgaccga cgtggaagag   120
gcgcagggca gcgcggtggc gaaggagatc gagcgcgccg cggcaaggc gctgttcctc   180 acgcaggacg tgaccgacga gagccgctgg gtcgaggtgg tcgagaaggc ccgcgcgcag   240
```

```
ttcggcggcc tgaacatcgt cgtcaacaac gccggcatcg gcaccgctgg cagcgccgag    300
gacgagacgc tggaggcctg cgccgcctg atgtccgtca acctcgacgg cgtcttcctc    360
ggcaccaagc acgcgatccg ggcgatgaag aacgggcccg gcacgggctc gatcatcaac    420
atctcgtcga tcgagggcat cgtcgccgac cccaagctcg cgtcctacaa cgccagcaag    480
ggcggcgtgc gcatcttctc gaagtcggcg gcactgcatt gcgcgcaggc gggctaccgc    540
atccgggtta acaccatcca tccgggctac atctggacgc cgatggtcga aggctatctg    600
accagcctcg gcgatgtcga gggtgggcgc caggtcatct cgaagatgca cccgatcggg    660
cggatgggtg agcccgacga catcgcctac ggtgtgctct acctgggctc cgacgagtcc    720
tcgttcatga cgggcagcga gctggtcatc gacggcggct acaccgcgca atag          774

<210> SEQ ID NO 10
<211> LENGTH: 756
<212> TYPE: DNA
<213> ORGANISM: Mesorhizobium sp.

<400> SEQUENCE: 10
atgactggtg aattcaagga caaggttgcg ctcgtcacag gagccggctc ggggataggg     60
gccgcaatcg ctcgcgaact ggccacagga ggcgccgagc tggtcgtcgc cgacctggag    120
cgggagtctg cgaacaggat cgtggaagga atccgagcga gtggaggccg agcccacgcc    180
tttgccgtgg atgtagccga cgccgaggcg gtcgagcgca tggtggattt tgccgttcgc    240
acgtgcggtg accttcatct ggcggtcaat aatgctggga tcggcggccc aagcgaaccg    300
accgccgact atccgctcga cggctggcgc aaggtgatcg atgtcaatct gaatggcgtc    360
ttctatggca tgaaatatga gatcgcagcg atactgaaat ccggcggcgg cgccatcgtg    420
aacatggcat ccatcctcgg ttcagtggga tttgcgaatg cctgcgccta tgtctccgcg    480
aaacacgcgc tgctgggact gacaaaaacg gcggcgatgg agtatgcggc acaaggcgtg    540
cgcatcaatg cggtcgggcc agctttcatc gacacgccgc ttctgtcgaa aaacctcgac    600
gaccaagtcc tcggccagct cgcgggactt catcccatcg gccggctcgg cacgcctgag    660
gaggtctcgg cgctcacctg tttcttgctt tccggacgcg cgagcttcat caccggcagt    720
tatcatctcg tcgatggcgg ctacaccacc cggtaa                              756

<210> SEQ ID NO 11
<211> LENGTH: 792
<212> TYPE: DNA
<213> ORGANISM: Streptomyces coelicolor

<400> SEQUENCE: 11
atgagcacca ccggaaccac ccccgccacc accgggtacg ccgccgagtt cgccggccgt     60
accgccctcg tcaccggtgc cgcctccggt atcggcctgg ccaccgcccg ccggctcggc    120 gccgcggcg cccgggtcgt cgtcgccgac ttcaacgccg agggcgccga aaggccgcc    180 gccgagctgc gggccggtgg cgtcgaggcc gccgcggtcg agctggacgt caccgtccg    240 gagtccgtcg aggcggccgt cgggttcgcc gtcgacacgt tcggctcgct ggacctcgcc    300
gtcaacaacg ccggcatcgg cggccccagc gccccgaccg gcgagtacga cgtgcggcc    360 taccagcgcg tcgtgcgcac caacctcgac ggcgtcttct actcgatgcg ctacgaactg    420
cccgccatcg aggcgccgg caagggcggc tcgatcgtga acgtcgcctc catcctcggc    480
tcggtcggct tcgccggctc ccccgcctac gtcgccgcca gcacggcgt ggtcgggctg    540
```

| | |
|---|---|
| acgaaggcgg ccgccgccga gtacgccgcc cgcggcatcc ggatcaacgc ggtcggtccg | 600 |
| ggcttcatcg acacccccct gctcaagacc atggacgagg ccgcctacaa ggggctggtc | 660 |
| gccctgcacc cggccggccg cctcgggcgc tccgaggagg tcgcggagct gatcgccttc | 720 |
| ctgctgtccg accgcgcgtc cttcgtcgcg ggcagctatc acctggtcga cggcgcctac | 780 |
| accgccgtct ga | 792 |

<210> SEQ ID NO 12
<211> LENGTH: 762
<212> TYPE: DNA
<213> ORGANISM: Ralstonia eutropha

<400> SEQUENCE: 12

| | |
|---|---|
| atgggagtaca tcgacatgaa gctcaaggac aaggtcgcca tcgtaacggg cggtgccagc | 60 |
| ggtattggcg aggcaacggt tcggctgttc gcttcccaag gtgccagcgt cgtcattgcc | 120 |
| gaccgctcgg cactcggcga gaagctcgcg cgtgaactga gcgaaagcag cttggccgcg | 180 |
| cactacagcg aagtcgatgt gtcgcgcgag acgacacgc gcaggctcat cgatgacacc | 240 |
| gtgagccgct cgggcggct cgacatcatg gtcgccaatg ccggcattgc gcatccgtct | 300 |
| gcaccagtcg aggatgtcag tgtcgagcaa tggcagcaga tgatcgacgt caacctgacc | 360 |
| ggcgtcttcc tgagcaacaa gcttgccatt gtgcagatga agaagcaggg caccggcggc | 420 |
| gcgatcgtca acatggcatc gatactcggg catgtcggga tgccgggcgc ggcgtcctac | 480 |
| aacgcggcaa agggcggcgt ggtcaacctc acgcgctctc tcggcgtctc gcatgcacag | 540 |
| gacggcatac gcgtcaacgc ggtatgtccg ggtttcgtgg caacaccgct gatcgaacgt | 600 |
| gccactgagg aagcccgtgc gcgcctggtg gcggcgcatc cgattggccg cctgggtcac | 660 |
| gccgatgagg tcgcgaaggc cgtgctgttt ctcgcgagcg acgatgcatc gttcatcgtc | 720 |
| ggtacgagcc tgatggtcga tggagggtat tgcgcgcaat ga | 762 |

<210> SEQ ID NO 13
<211> LENGTH: 759
<212> TYPE: DNA
<213> ORGANISM: Herpentosiphon aurantiacus

<400> SEQUENCE: 13

| | |
|---|---|
| atgaaccagt atgactttcg tggaaaagtg gcgcttgtca ccggcggcgc ctcggggatt | 60 |
| ggtgcggcgt gcgtgcatac ctttgcgcgt ggcggcgcga aggtcgcgat tgttgatcgc | 120 |
| aatcaggatc tgggcgcaca aaccgtggcg gcggtccgcg aggccggcgg cgatgcgatc | 180 |
| tttctcccgg tggatgtcgc ccaatcaggg gccgttgagg cgatggttac cgacaccatc | 240 |
| acggcctttg gacagctgga tattgcggtc aataatgccg ggatcggcgg cgagtctaat | 300 |
| cctaccggca cctacagcat tgaaggttgg cagacggtca ttgatgtgaa cctcaacggt | 360 |
| gtcttctatt gcatgcgcta cgaaattcca gccatgctgg cgcagggcgg cggcgtgatc | 420 |
| gtgaatatgg cctcgatcct agggactgtc ggatttgcgt cctccccagc ctatgtcgcc | 480 |
| gccaagcacg cggtggttgg tctcaccaag gccgccgccc tggactatgg cgccaaggg | 540 |
| ctgcggatca actcggtcgg gccgggcttt atcaaaacac cactgcttga cggtggcctg | 600 |
| gacgatcaga cccaaaccta tctgagcggg ctccacgccg tcggacgcat gggcgagtca | 660 |

```
gcggaagtcg cggcgctggt cgcctttctc tgctccgctg aggcctcatt cctgacgggt    720
ggctattatc tggtcgatgg tggatacacg gcgcaataa                           759

<210> SEQ ID NO 14
<211> LENGTH: 750
<212> TYPE: DNA
<213> ORGANISM: Paracoccus denitrificans

<400> SEQUENCE: 14
atggacattc gtttcgacaa caagatcgcc cttgtgaccg gcgccggctc ggggctgggc     60
gaggcgatag cgctggagct tgccgcctcg ggcgccacgg tggtggccgc cgacctgcat    120
gaagcgacag cccgcgccac cgccgacagg atcgtcgcgg cgggcggcaa ggccaaggcc    180
gtggcgggcg atgtctccga tcctgatgcg gtgcgcaagg ccgtcgaggt cgccaagggg    240
ctgggcgggc tgcacctgct ggtgaacaat gccggcatcg gcggcccccag cgcgccggtc    300 ggggactatc cgctggacgg ctggaaaaag gtcatcgacg tcaacctgaa cgcggtcttc    360
tacggcatgc gctacgggat tccggcgatg ctggacgcgg gcgcggggc gatcgtgaac    420 atggcctcga tcctgggctc ggtcgggttc aacggcgcgg gcgcctatgt ctcggccaag    480
catgccgtgg tgggcatgac caagaacgcg gcgctggaat atgcgcaaaa gggcatccgg    540
gtgaactcgg tcggcccggc cttcatcgac acgccgctgc tcgaccagtt ggacagcgac    600
accaggcagg cgctggtcgg ccgccatccc atcgccggc tgggccgggc ggacgaggtt    660
gcggggcttg tcgtgttcct gctttcggac cgcgccagct tcatcaccgg cagctatcac    720
ctggtggatg gcggctatac ggcgctgtga                                    750
```